(12) United States Patent
McKenna

(10) Patent No.: US 10,688,177 B2
(45) Date of Patent: *Jun. 23, 2020

(54) NATURALLY-OCCURRING CPG OLIGONUCLEOTIDE COMPOSITIONS AND THERAPEUTIC APPLICATIONS THEREOF

(71) Applicant: LABYRINTH HOLDINGS, LLC, Houston, TX (US)

(72) Inventor: Elizabeth McKenna, Houston, TX (US)

(*) Notice: Subject to any disclaimer, the term of this patent is extended or adjusted under 35 U.S.C. 154(b) by 71 days.

This patent is subject to a terminal disclaimer.

(21) Appl. No.: 15/862,209

(22) Filed: Jan. 4, 2018

(65) Prior Publication Data

US 2018/0369367 A1 Dec. 27, 2018

Related U.S. Application Data

(63) Continuation of application No. 14/640,075, filed on Mar. 6, 2015, now Pat. No. 9,931,398, which is a continuation of application No. 14/034,044, filed on Sep. 23, 2013, now abandoned, and a continuation-in-part of application No. 13/743,194, filed on Jan. 16, 2013, now Pat. No. 9,713,630.

(60) Provisional application No. 61/704,090, filed on Sep. 21, 2012, provisional application No. 61/586,975, filed on Jan. 16, 2012.

(51) Int. Cl.

| A61K 39/39 | (2006.01) |
| C12N 15/117 | (2010.01) |
| A61K 35/74 | (2015.01) |
| A61K 45/06 | (2006.01) |
| A61K 9/00 | (2006.01) |
| A61K 39/00 | (2006.01) |

(52) U.S. Cl.
CPC .............. *A61K 39/39* (2013.01); *A61K 9/006* (2013.01); *A61K 35/74* (2013.01); *A61K 45/06* (2013.01); *C12N 15/117* (2013.01); *A61K 2039/522* (2013.01); *A61K 2039/55561* (2013.01); *C12N 2310/17* (2013.01); *C12N 2330/00* (2013.01); *C12N 2330/10* (2013.01); *Y02A 50/401* (2018.01)

(58) Field of Classification Search
None
See application file for complete search history.

(56) References Cited

U.S. PATENT DOCUMENTS

| 3,806,290 A | 4/1974 | Graff et al. |
| 4,322,405 A | 3/1982 | Schulthess et al. |
| 5,716,615 A | 2/1998 | Vesely et al. |
| 5,955,321 A | 9/1999 | Bijl et al. |
| 6,194,388 B1 | 2/2001 | Krieg et al. |
| 6,207,646 B1 | 3/2001 | Krieg et al. |
| 6,214,806 B1 | 4/2001 | Krieg et al. |
| 6,218,371 B1 | 4/2001 | Krieg et al. |
| 6,239,116 B1 | 5/2001 | Krieg et al. |
| 6,281,191 B1 | 8/2001 | Slesarev et al. |
| 6,339,068 B1 | 1/2002 | Krieg et al. |
| 6,767,557 B2 | 7/2004 | Ulrich et al. |
| 7,265,152 B2 | 9/2007 | Saha et al. |
| 7,959,911 B2 | 6/2011 | Desimone |
| 8,007,783 B2 | 8/2011 | Miller |
| 8,278,089 B2 | 10/2012 | Miller |
| 8,304,226 B2 | 11/2012 | Miller |
| 9,931,398 B2 | 4/2018 | McKenna et al. |
| 2002/0164341 A1 | 11/2002 | Davis et al. |
| 2004/0129174 A1 | 7/2004 | Bunick et al. |
| 2005/0124053 A1 | 6/2005 | Moen et al. |
| 2007/0179101 A1 | 8/2007 | Kitagawa et al. |
| 2008/0045473 A1 | 2/2008 | Uhlmann et al. |
| 2008/0050353 A1 | 2/2008 | Miller et al. |
| 2009/0297561 A1 | 12/2009 | Pasternack et al. |
| 2011/0104134 A1 | 5/2011 | Ihara et al. |

FOREIGN PATENT DOCUMENTS

| EP | 1178118 | 2/2002 |
| EP | 1920774 | 5/2008 |
| FR | 2951377 | 4/2011 |
| JP | H04264034 | 9/1992 |
| JP | H0656680 | 3/1994 |
| JP | 09301878 | 11/1997 |
| JP | H09301877 | 11/1997 |
| JP | H1086 | 1/1998 |
| JP | 2000004830 | 1/2000 |
| JP | 2002332242 | 11/2002 |
| JP | 2005237328 | 2/2004 |
| JP | 2005247780 | 9/2005 |
| JP | 2006507362 | 3/2006 |

(Continued)

OTHER PUBLICATIONS

"Fundamentals of Freeze-Drying," Pharm. Biotechnol., 14:281-360 (2002).
"Nitric oxide synthesis protects against oxidative stress: Bacillus Subtilis Bacterium". Online:http://www.asknature.org/strategy/2a2bf810dc95e1eebc2d1d1055fba0ec#.UxV6XfldVIF.
Becker, "CpG ODNs treatments of HIV-1 infected patients may cause the decline of transmission in high risk populations—a review, hypothesis and implications," Virus Genes 30(2):251-66 (2005).
Beutler et al., "Synergy between TLR2 and TLR4: a safety mechanism," Blood Cells Mol Dis. 27(4):728-30. (2001).
Bressanelli et al., "Structural Analysis of the Hepatitis C Virus RNA Polymerase in Complex with Ribonucleotides," Journal of Virology 76(7):3482-3492 (2002).

(Continued)

Primary Examiner — Brian Gangle
(74) Attorney, Agent, or Firm — McDonnell Boehnen Hulbrt & Berghoff LLP

(57) ABSTRACT

The present invention relates to combination therapies for the treatment of a variety of disorders in mammals, including hepatic disorders and cancer. The combination of agents includes naturally-occurring (versus synthetic) oligonucleotides, particularly immunostimulatory oligodeoxynucleotides such as CpG ODNs, obtained from a natural source and one or more extracts from a Gram positive bacteria, such as *Lactobacillus* spp.

20 Claims, 5 Drawing Sheets

Specification includes a Sequence Listing.

(56) References Cited

FOREIGN PATENT DOCUMENTS

| JP | 2009280606 | 12/2009 |
|---|---|---|
| JP | 2010504278 | 2/2010 |
| JP | 201168643 | 4/2011 |
| JP | 2011516521 | 5/2011 |
| JP | 2012502026 | 1/2012 |
| WO | WO 98/40100 | 9/1998 |
| WO | 2003015711 | 2/2003 |
| WO | 2003026688 | 4/2003 |
| WO | WO 2004037182 | 5/2004 |
| WO | 2007013613 | 2/2007 |
| WO | 2008000783 | 1/2008 |
| WO | 2009124954 | 10/2009 |
| WO | 2010001509 | 1/2010 |
| WO | 2010027344 | 3/2010 |
| WO | WO 2010144943 | 8/2011 |
| WO | 2011151431 | 12/2011 |
| WO | 2013109635 | 7/2013 |
| WO | WO2014/047588 | 3/2014 |

OTHER PUBLICATIONS

Ceprnja et al. "Oxidative Stress Markers in patients with post-traumatic stress disorder. "Collegium Antropologicum,"" 35(4):1155-60 (2011).

Forsyth et al., "Lactobacillus GG treatment ameliorates alcohol-induced intestinal oxidative stress, gutleakiness, and liver injury in a rat model of alcoholic steatohepatitis," Alcohol 43(2): 163-172 (2009).

Fukata et al., "Toll-like receptors (TLRs) and Nod-like receptors (NLRs) in inflammatory disorders," Seminars in Immunology 21:242-253 (2009).

Galey et al., "The in vitro permeability of skin and buccal mucosa to selected drugs and tritiated water," J Invest Dermatol. 67(6):713-7 (1976).

Galigniana et al. "Regulation of the glucocorticoid response to stress-relateddisorders by the Hsp90-binding immunophilin FKBP51," Journal of Neurochemistry 122:4-18 (2012).

Golovina et al., "Specific binding of glucosaminylmuramyl peptides to histones," FEBS Lett. 454(1-2):152-6 (1999).

Hacker et al., "CpG-DNA-specific activation of antigen-presenting cells requires stress kinase activity and is preceded by non-specific endocytosis and endosomal maturation," EMBO J.17(21):6230-40 (1998).

Hartmann et al., "CpG DNA: a potent signal for growth, activation, and maturation of human dendritic cells," Proc Natl Acad Sci USA 96(16):9305-10 (1999).

Krieg et al, "CpG motifs in bacterial DNA trigger direct B-cell activation," Nature, vol. 374, pp. 546-549 (1995).

Kumar et al., "Cancer-preventing attributes of probiotics: an update," Int J Food Sci Nutr. 61(5):473-96 (2010).

Laman et al., "Identification of pentadecapeptide mimicking muramyl peptide," Vaccine 25(15):2900-2906 (2006).

Lipford et al., "Bacterial DNA as immune cell activator," Trends Microbiol. 6(12):496-500 (1998).

Maletzki Claudia et al. "Bacterial Immunotherapy-Antitumoral Potential of the Streptococcal Toxin Streptolysin S-," Pancreatic Cancer-Clinical Management, Prof. Sanjay Srivastava, 163-176 (2012).

Messina et al., "Stimulation of in vitro murine lymphocyte proliferation by bacterial DNA," J. Immunol. 147:1759-1764 (1991).

Peng et al., "Protective effects of Lactobacillus plantarum NDC 75017 against lipopolysaccharide-induced liver injury in mice," Inflammation 37(5):1599-607 (2014).

Pineda et al., "A randomized, double-blinded, placebo-controlled pilot study of probiotics in active rheumatoid arthritis," Med Sci Monit.17(6):CR347-54 (2011).

Pinegin et al., "The occurrence of natural antibodies to minimal component of bacterial cell wall (N-acetylglucosaminyl-N-acetylmuramyl dipeptide) in sera from healthy humans," Immunol Lett. 47(1-2):33-7 (1995).

Pisetsky, "The immunologic properties of DNA," J Immunol. 156(2):421-3 (1996).

Rachmilewitz et al., "Toll-like receptor signaling mediates the anti-inflammatory effects of probiotics in murine experimental colitis," Gastroenterology 126(2):520-8 (2004).

Rau, "Adalimumab (a fully human anti-tumour necrosis factor alpha monoclonal antibody) in the treatment of active rheumatoid arthritis: the initial results of five trials," Ann Rheum Dis. 61 Suppl 2:ii70-3 (2002).

Reis et al. "LPS-induced formation of immunoproteasomes: TNF-$\alpha$ and nitric oxide production are regulated by altered composition of proteasome-active sites," Cell Biochem Biophys 60(1-2):77-88 (2011).

Siebler et al., "Immunization with the immunoregulatory saprophytic bacterium, *Mycobacterium vaccae*, enhances fear extinction in adult male Sprague Dawley rats," 24th Annual Meeting of the InternationalBehavioral Neuroscience Society 24:82 (2015).

Squier et al., "Lipid Content and Water Permeability of Skin and Oral Mucosa," J Invest Dermatol. 96(1):123-6 (1991).

Te et al., "Mechanism of action of ribavirin in the treatment of chronic hepatitis C," Gastroenterol. Hepatol., 3:218-225 (2007).

Tokunaga et al., "Antitumor activity of deoxyribonucleic acid fraction from *Mycobacterium bovis* BCG. I. Isolation, physicochemical characterization, and antitumor activity," J Natl Cancer Inst 72(4):955-62 (1984).

Vollmer et al., "Immunotherapeutic applications of CpG oligodeoxynucleotide TLR9 agonists," Advanced Drug Delivery Reviews 61(3):195-204 (2009).

Weeratna et al., "Potential use of CpG ODN for cancer immunotherapy. 18-20Update on cancer therapeutic," Update on Cancer Therapeutics 1(1):49-58 (2006).

Yi, et al., "CpG oligodeoxyribonucleotides rescue mature spleen B cells from spontaneous apoptosis and promote cell cycle entry," J Immunol. 160(12):5898-906 (1998).

Zhang et al., "CpG ODN pretreatment attenuates concanavalin A-induced hepatitis in mice," Int Immunopharmacol (1):79-85 (2010).

Zimmerman et al., "Post-traumatic anxiety associates with failure of the innate immune receptor TLR9 to evade the pro-inflammatory NFκB pathway," Transl Psychiatry 2(2): e78 (2012).

Zou et al. "An APAF-1.cytochrome c multimeric complex is a functional apoptosome that activates procaspase-9," J Biol Chem. 274(17):11549-56 (1999).

Zuezem et al., "Peginterferon alfa-2a in patients with chronic hepatitis," N Engl J Med. 343(23):1666-72 (2000).

International Preliminary Report on Patentability corresponding to Application No. PCT/US2013/021752; dated May 15, 2013 pp. 1-7.

International Search Report for corresponding International patent application No. PCT/US 2013/061236, dated Jan. 16, 2014, pp. 1-9.

International Preliminary Report on Patentability corresponding to Application No. PCT/US 2013/061236; dated Mar. 24, 2015 pp. 1-12.

Written Opinion for corresponding International patent application No. PCT/US 2013/061236; dated Dec. 12, 2013, pp. 1-11.

International Search Report and Written Opinion for corresponding International patent application No. PCT/US2016/061247, dated Jan. 26, 2017, pp. 1-16.

International Search Report for corresponding International patent application No. PCT/US2013/021752, dated May 15, 2013.

Written Opinion for corresponding International patent application No. PCT/US2013/021752, dated May 15, 2013.

Krieg, "Mechanisms and applications of immune stimulatory CpG oligodeoxynucleotides," Biochim. Biophys. Acta, 1489: 107-116 (1999).

Tokunaga et al., "A synthetic single-stranded DNA, poly(dG,dC), induces interferon-alpha/beta and -gamma, augments natural killer activity, and suppresses tumor growth," Jpn. J. Cancer Res. 79:682-686 (1988).

Hu et al., "WD-40 repeat region regulates Apaf-1 self-association and procaspase-9 activation," J Biol Chem. 273 (50)33489-94 (1998).

(56) References Cited

OTHER PUBLICATIONS

Iliev et al., "Strong immunostimulation in murine immune cells by Lactobacillus rhamnosus GG DNA containing novel oligodeoxynucleotide pattern" Cell Microbiol. 7(3):403-14 (2005).
Inohara et al., "Nod1, an Apaf-1-like activator of caspase-9 and nuclear factor-kappaB," J Biol Chem. 274 (21):14560-7 (1999).
Kim et al., "Probiotic genomic DNA reduces the production of pro-inflammatory cytokine tumor necrosis factor-alpha," FEMS Microbiol Lett.328(1):13-9 (2012).
Kozlov et al., Effect on human complement of blastolysin and the glycopeptide (MDP and GMDP) and carbohydrate fragments of peptidoglycans, Bioorg Khim. 11(11):1510-8 (1985).
Kerkmann et al., "Spontaneous formation of nucleic acid-based nanoparticles is responsible for high interferon-alpha induction by CpG-A in plasmacytoid dendritic cells," J Biol. Chem. 280(9):8086-93 (2005).
Krieg, "Toll-like receptor 9 (TLR9) agonists in the treatment of cancer," Oncogene 27, 161-167 (2008).
Krieg, Applied Oligonucleotide Technology, C. A. Stein and A. M. Krieg, (Eds.), John Wiley and Sons, Inc., New York, N.Y., pp. 431-448 (1998).
Adamberg et al, "The effect of temperature and pH on the growth of lactic acid bacteria: a pH-auxostat study," Int J Food Microbiol. 85(1-2):171-83 (2003).
Ayers et al., "Ability of streptococci to survive pasteurization," Journal of Agricultural Research, vol. 2, No. 4, p. 321-330 (1914).
Blanton et al., "Probiotics Blunt the Anti-Hypertensive Effect of Blueberry Feeding in Hypertensive Rats without Altering Hippuric Acid Production," PLoS One 10(11):(1-14) (2015).
Chapot-Chartier et al., "Cell wall structure and function in lactic acid bacteria," Microb Cell Fact. 13 Suppl 1:S9 (2014).
Chassy et al., "Method for the lysis of Gram-positive, asporogenous bacteria with lysozyme," Appl Environ Microbiol. 39(1):153-8 (1980).
Corzo, "Time, the forgotten dimension of ligand binding teaching," Biochem Mol Biol Educ 34(6):413-6 (2006).
Eckner et al., "Potential for the Low-Temperature Pasteurization of Dairy Fluids Using Membrane Processing," Journal of Food Protection, vol. 54, No. 10, pp. 793-797 (1991).
Mikelsaar et al., "Lactobacillus fermentum ME-3—an antimicrobial and antioxidative probiotic," Microb Ecol Health Dis. 21(1):1-27 (2009).
Mohammadi et al., "Effects of Probiotics on Biomarkers of Oxidative Stress and Inflammatory Factors in Petrochemical Workers: A Randomized, Double-blind, Placebo-controlled Trial," Int J Prev Med. 2015; 6:82 (2015).
Ragland et al., "From bacterial killing to immune modulation: Recent insights into the functions of lysozyme," PLoS Pathog. 13(9) (2017).
U.S. Department of Health and Human Services "Grade "A" Pasteurized Milk Ordinance," 2009 Revision (p. 1-382).
Vorobjeva, "Propionibacteria," Springer Science & Business Media, p. 149 (1999).
Wikipedia: "Pasteurization," retrieved from the Internet:URL:https://en.wikipedia.org/wiki/Pasteurization [retrieved on Jul. 26, 2018] (pp. 1-11).
International Preliminary Report on Patentability corresponding to Application No. PCT/US2016/061247, dated May 15, 2018, pp. 1-10.
Basu et al., "Raised levels of F(2)-isoprostanes and prostaglandin F(2alpha) in different rheumatic diseases," Ann Rheum Dis. 60(6):627-31 (2001).
Halliwell et al., "Measuring reactive species and oxidative damage in vivo and in cell culture: how should you do it and what do the results mean?" Br J Pharmacol. 142(2):231-55 (2004).
Lecat et al., "The protein Nod2: an innate receptor more complex than previously assumed," Biochem Pharmacol. 80 (12):2021-31 (2010).
Testro et al., "Toll-like receptors and their role in gastrointestinal disease," J Gastroenterol Hepatol. 24(6):943-54 (2009).
Tran et al., "Immune response following vaccination against *Salmonella enteritidis* using 2 commercial bacterins in laying hens," Canadian Journal of Veterinary Research, 74(3):185-192(8) (2010).
Bartlett et al., "Understanding the Oral Mucosal Absorption and Resulting Clinical Pharmacokinetics of Asenapine," AAPS PharmSciTech, vol. 13, No. 4 (2012).
Coakley et al., "Conjugated linoleic acid biosynthesis by human derived *Bifidobacterium* species," Journal of Applied Microbiology 94: 138-145 (2003).
Inagawa et al., "Oral administration of lipopolysaccharides for the prevention of various diseases: benefit and usefulness," Anticancer Res., 31(7):2431-6 (2011).
Ivanov et al., "Structure, design, and synthesis of immunoactive peptides," Pure & Appl. Chem., vol. 59, No. 3, pp. 317-324 (1987).
Kullisaar et al., "Two antioxidative lactobacilli strains as promising probiotics," Int J Food Microbial. 72(3):215-24 (2002).
Kullisaar et al., "Antioxidative probiotic fermented goats' milk decreases oxidative stress-mediated atherogenicity in human subjects," Br J Nutr.90(2):449-56 (2003).
Meshcheryakova et al., "Evidence for correlation between the intensities of adjuvant effects and NOD2 activation by monomeric, dimeric and lipophylic derivatives of N-acetylglucosaminyl-N-acetylmuramyl peptides," Vaccine 25 (23):4515-20 (2007).
Namba et al., "Effect of oral administration of lysozyme or digested bacterial cell walls on immunostimulation in guinea pigs," Infect Immun. Feb;31(2):580-3 (1981).
Naang et al., "Sublingual mucosa as a route for systemic drug delivery," International Journal of Pharmacy and Pharmaceutical Sciences 3:18-22 (2001).
Sasmaz et al., "Rubella seroprevalence in women in the reproductive period, Mersin, Turkey," Vaccine. 25(5):912-7 (2006).
Schroder et al., "Lipoteichoic acid (LTA) of *Streptococcus pneumoniae* and *Staphylococcus aureus* activates Immune cells via Toll-like receptor (TLR)-2, lipopolysaccharide-binding protein (LBP), and CD14, whereas TLR-4 and MD-2 are not involved," J Biol Chem. 278(18):15587-94 (2003).
Seikagaku, "Structure and function of cytoplasmic pattern recognition receptor NLR," The Journal of Japanese Biochemical Society, vol. 82 (1), pp. 12-20 (2010). (English machine translation).
Takahashi et al., "Immune Response of Mice to Orally Administered Lactic Acid Bacteria," Bioscience, Biotechnology, and Biochemistry, 57:9, p. 1557-1560 (1993).
Vauterin et al. 2000 (Synopsis on the Taxonomy of the Genus *Xanthomonas*; The American Phytopathological Society; Pub. No. P-2000-056-010; vol. 90, No. 7, p. 677) (2000).
Yamamoto et al., "Role of Nod2 in the development of Crohn's disease," Microbes and Infection, vol. 11 (12):912-918 (2009).
Yamamoto (Ed.), "Basic Pharmaceutical Science Textbook Series 10: Immunology," H Kagakudojin Co., Ltd., Apr. 20, 2012, 1st edition, 4th issue, pp. 156-159, pp. 230 (English machine translation).
Zufall et al., "The Biological Impact of Flash Pasteurization Over a Wide Temperature Interval," Journal of the Institute of Brewing 106(3): 163-167 (2000).
Silhavy et al., "The bacterial cell envelope," Cold Spring Harb Perspect Biol., 2(5):a000414 (2010).

Human TLR/NLR Ligand Screening

Screening #1

| TLR/NLR Cell Line | No Ligand | Lysate 1/100 | Control + |
|---|---|---|---|
| hTLR2 | 0.114 | 2.188 | 2.052 |
| hTLR3 | 0.130 | 0.166 | 2.438 |
| hTLR4(MD2-CD14) | 0.183 | 0.399 | 1.900 |
| hTLR5 | 0.099 | 0.126 | 2.392 |
| hTLR7 | 0.161 | 0.185 | 2.119 |
| hTLR8 | 0.082 | 0.084 | 2.237 |
| hTLR9 | 0.153 | 0.184 | 1.984 |
| hNOD1 | 0.068 | 0.057 | 1.736 |
| hNOD2 | 0.159 | 1.504 | 1.326 |

Screening #2

| TLR/NLR Cell Line | No Ligand | Lysate 1/100 | Control + |
|---|---|---|---|
| hTLR2 | 0.093 | 2.173 | 2.046 |
| hTLR3 | 0.116 | 0.160 | 2.425 |
| hTLR4(MD2-CD14) | 0.140 | 0.301 | 1.848 |
| hTLR5 | 0.093 | 0.121 | 2.347 |
| hTLR7 | 0.158 | 0.160 | 2.081 |
| hTLR8 | 0.085 | 0.092 | 2.228 |
| hTLR9 | 0.144 | 0.186 | 2.083 |
| hNOD1 | 0.070 | 0.058 | 1.765 |
| hNOD2 | 0.172 | 1.249 | 1.335 |

Screening #3

| TLR/NLR Cell Line | No Ligand | Lysate 1/100 | Control + |
|---|---|---|---|
| hTLR2 | 0.119 | 2.140 | 1.980 |
| hTLR3 | 0.123 | 0.141 | 2.441 |
| hTLR4(MD2-CD14) | 0.135 | 0.302 | 1.870 |
| hTLR5 | 0.093 | 0.120 | 2.333 |
| hTLR7 | 0.148 | 0.138 | 2.003 |
| hTLR8 | 0.083 | 0.073 | 2.158 |
| hTLR9 | 0.152 | 0.169 | 1.954 |
| hNOD1 | 0.069 | 0.062 | 1.791 |
| hNOD2 | 0.170 | 1.597 | 1.321 |

FIG. 5

Screening #1

| Control Cell Line | No Ligand | Lysate 1/100 | TNFa |
|---|---|---|---|
| HEK293/Null1 | 0.070 | 0.083 | 1.962 |
| HEK293/Null-k | 0.133 | 0.112 | 1.820 |
| HEK293/Null2 | 0.097 | 0.081 | 1.607 |

Screening #2

| Control Cell Line | No Ligand | Lysate 1/100 | TNFa |
|---|---|---|---|
| HEK293/Null1 | 0.070 | 0.089 | 1.961 |
| HEK293/Null-k | 0.130 | 0.112 | 1.778 |
| HEK293/Null2 | 0.097 | 0.078 | 1.619 |

Screening #3

| Control Cell Line | No Ligand | Lysate 1/100 | TNFa |
|---|---|---|---|
| HEK293/Null1 | 0.068 | 0.069 | 1.985 |
| HEK293/Null-k | 0.129 | 0.199 | 1.809 |
| HEK293/Null2 | 0.099 | 0.086 | 1.636 |

FIG. 6

SEQUENCE LISTING

```
<160> NUMBER OF SEQ ID NOS: 1

<210> SEQ ID NO 1
<211> LENGTH: 24
<212> TYPE: DNA
<213> ORGANISM: Artificial Sequence
<220> FEATURE:
<223> OTHER INFORMATION: Synthetic

<400> SEQUENCE: 1
tcgtcgtttt gtcgttttgt cgtt                                          24
```

NATURALLY-OCCURRING CPG OLIGONUCLEOTIDE COMPOSITIONS AND THERAPEUTIC APPLICATIONS THEREOF

CROSS REFERENCE TO RELATED APPLICATIONS

This application is a continuation of U.S. patent application Ser. No. 14/640,075, filed Mar. 6, 2015, which is a continuation of U.S. patent application Ser. No. 14/034,044, filed Sep. 23, 2013, which claims priority to U.S. Provisional Patent application Ser. No. 61/704,090, filed Sep. 21, 2012, this application is a continuation in part of U.S. patent application Ser. No. 13/743,194 filed Jan. 16, 2013, which claims priority to U.S. Provisional Patent application Ser. No. 61/586,975, filed Jan. 16, 2012, the contents of which are incorporated herein by reference in its entirety.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

Field of the Invention

The inventions disclosed and taught herein relate generally to combinations and methods of treating disorders in mammals, particularly humans. In particular, this invention provides combination therapies and treatment regimens for the treatment of hepatic disorders and human immunodeficiency virus (HIV) using a naturally-occurring immunostimulatory oligodeoxynucleotide and a cell-wall fraction of a gram positive bacteria.

Description of the Related Art

A traditional approach to treating hepatic disorders, as well as a number of other viral disorders in mammals, is to target the virus itself with therapy, such as with virus specific chemotherapeutic agents. An alternative approach to treating such disorders is to target the immune system of the subject ("immunotherapy"), rather than, or in addition to, targeting the virus itself. A potential benefit of immunotherapy is to provide improved efficacy by enhancing the patient's own immune response to tumors while minimizing deleterious effects to normal, healthy cells.

Bacterial DNA has immune stimulatory effects to activate B cells and natural killer cells [Tokunaga, T., et al., 1988. Jpn. J. Cancer Res. 79:682-686; Tokunaga, T., et al., 1984, JNCI 72:955-962; Messina, J. P., et al., 1991, J. Immunol. 147:1759-1764, and reviewed in Krieg, 1998, In: *Applied Oligonucleotide Technology*, C. A. Stein and A. M. Krieg, (Eds.), John Wiley and Sons, Inc., New York, N.Y., pp. 431-448]. The immune stimulatory effects of bacterial DNA are a result of the presence of unmethylated CpG dinucleotides in particular base contexts (CpG motifs), which are common in bacterial DNA, but methylated and underrepresented in vertebrate DNA [Krieg et al, Nature, Vol. 374, pp. 546-549 (1995); Krieg, Biochim. Biophys. Acta, 93321:1-10 (1999)]. The immune stimulatory effects of bacterial DNA can be mimicked with synthetic oligodeoxynucleotides (ODN) containing these CpG motifs (referred to interchangeably hereinbelow as "CpG ODNs" or "immunostimulatory ODNs"). Such CpG ODNs have been shown to have high stimulatory effects on a number of mammalian biological functions, inducing B cell proliferation, cytokine and immunoglobulin secretion, natural killer (NK) cell lytic activity, IFN-γ secretion, and activation of dendritic cells (DCs) and other antigen presenting cells to express costimulatory molecules and secrete cytokines, especially the Th1-like cytokines that are important in promoting the development of Th1-like T cell responses. The immune stimulatory effects of native phosphodiester backbone CpG ODN are highly CpG specific in that the effects are dramatically reduced if the CpG motif is methylated, changed to a GpC, or otherwise eliminated or altered [see, Krieg, et al, Nature, Vol. 374, pp. 546-549 (1995); Hartmann, et al, 1999 Proc. Natl. Acad. Sci. USA, Vol. 96, pp. 9305-9310 (1999)].

It was previously thought that the immune stimulatory effects required the CpG motif in the context of a purine-purine-CpG-pyrimidine-pyrimidine sequence [Krieg, et al., Nature, Vol. 374, pp. 546-549 (1995); Pisetsky, J. Immunol., Vol. 156, pp. 421-423 (1996); Hacker, et al., EMBO J., Vol. 17, pp. 6230-6240 (1998); Lipford, et al., Trends in Microbiol. 6:496-500(1998)]. However, it is now clear that mouse lymphocytes respond quite well to phosphodiester CpG motifs not in this context [Yi, et al., J. Immunol. Vol. 160, pp. 5898-5906(1998)] and the same is true of human B cells and dendritic cells [Hartmann, et al., Proc. Natl. Acad. Sci. USA, 96, pp. 9305-10 (1999)].

One class of GpG ODN is potent for activating B cells but is relatively weak in inducing IFN-alpha and NK cell activation; this class has been termed the B class. The B class CpG oligonucleotides typically are fully stabilized and include an unmethylated CpG dinucleotide within certain preferred base contexts. See, e.g., U.S. Pat. Nos. 6,194,388; 6,214,806; 6,239,116; and 6,339,068.

It has also been shown that T cell-mediated hepatic damage plays a key role in the pathogenesis of liver diseases such as autoimmune hepatitis, viral hepatitis and acute liver failure [Becker, Y., Virus Genes, Vol. 30 (2), pp. 251-266 (2005)]. CpG-containing oligodeoxynucleotides (CpG ODN), a ligand for toll-like receptor (TLR) 9, is widely used as an immunological adjuvant, and several groups have reported on the results of their investigations of the effect of CpG ODN on T cell-mediated liver injury in murine models of hepatitis and other diseases. It has also been shown that the activation of inflammatory cells can be diminished by CpG ODN pretreatment. These results suggested that CpG ODN pretreatment protects from liver injury via inhibiting hepatocyte apoptosis, inflammation and activation of lymphocytes [Zhang, H., et al., Int. Immunopharmacol., Vol. 10(1), pp. 79-85 (2010)].

Although the individual use of CpG ODNs to induce therapeutic response hold great promise in the treatment of a number of disorders in patients, there remains a need to develop novel therapies to treat such disorders with such immunotherapeutic approaches.

The inventions disclosed and taught herein are directed to therapies and treatment regimens for the treatment of hepatic disorders, cancer, lyme disease, and/or human immunodeficiency virus (HIV), as well as compositions for such methods of treatment using a naturally-occurring immunostimulatory oligodeoxynucleotide and a cell-wall fraction of a gram positive bacteria.

BRIEF SUMMARY OF THE INVENTION

The objects described above and other advantages and features of the invention are incorporated in the application as set forth herein, and the associated appendices and drawings, related to systems for the use of combination therapies and treatment regimens for the treatment of immune diseases and disorders, including hepatic disorders, cancer, and human immunodeficiency virus (HIV) disorders, as well as cancer disorders, using a naturally-occurring immunostimulatory oligodeoxynucleotide and a cell-wall fraction of at least one gram positive bacteria.

In accordance with a first embodiment of the present disclosure, a method of treating or preventing one or more disorders in a patient in need of such treatment is described, wherein the method comprises (a) a therapeutic regimen comprising administering to the patient, simultaneously, semi-simultaneously, separately or sequentially a therapeutically effective amount of one or more naturally-occurring CpG OGNs in combination with a therapeutically effective amount of one or more gram-positive bacterial lysates; and, optionally (b) administering to the patient a maintenance regimen comprising a maintenance dose of a CpG OGN, a gram-positive bacterial lysate, or a combination thereof. In an exemplary embodiment, the CpG ODN is a naturally occurring CpG ODN, which in accordance with certain aspects of the disclosure, comes from the gram-positive bacterial lysate. In further aspects of the disclosure, the therapeutic regimen may further include a therapeutically effective amount of a synthetic CpG ODN, or a CpG ODN from a source separate from the bacterial lysate.

In accordance with a further embodiment of the present disclosure, a composition for use in treating or preventing one or more disorders in a patient in need of such treatment is described, wherein the composition comprises a therapeutically effective amount of a bacterial cell-wall lysate or fraction, and a therapeutically effective amount of a naturally-occurring CpG ODN.

In yet another embodiment of the present disclosure, compositions for delivery of a therapeutic agent across the mucosa of a subject for the treatment of a hepatic disorder in the subject are described, the composition comprising (a) a lysate or cell wall extract derived from or isolated from one or more gram-positive bacteria, or a pharmaceutically acceptable salt thereof; and (b) a naturally-occurring immunostimulatory oligodeoxynucleotide (ODN); wherein the cell wall lysate and the ODN are present in an amount effective to treat an immune disorder. In accordance with aspects of this embodiment, the composition is a dietary supplement.

In accordance with further embodiments of the present disclosure, compositions for the treatment of complications of a hepatic disorder in a subject suffering from one or more hepatic disorders are described, the composition comprising a therapeutically effective amount of a lysate or cell wall extract derived from or isolated from one or more gram-positive bacteria, or a pharmaceutically acceptable salt thereof; and at least one Toll Like receptor (TLR) 9 agonist, the gram-positive bacteria being selected from the *Lactobacillus* family of bacteria. In accordance with aspects of this embodiment, the TLR 9 agonist is a CpG oligodeoxynucleotide (CpG ODN). In further accordance with aspects of this embodiment, the CpG ODN is naturally-occurring within the bacterial lysate.

In another embodiment of the present disclosure, methods of inducing an immune response to a tumor in a subject are described, the method comprising selecting a subject with a tumor; and administering to the subject a therapeutically effective amount of a composition comprising (a) a lysate or cell wall extract derived from or isolated from one or more gram-positive bacteria, or a pharmaceutically acceptable salt thereof; and (b) a naturally-occurring CpG oligodeoxynucleotide (ODN), thereby inducing the immune response to the tumor in the subject. In accordance with select aspects of this embodiment, the naturally-occurring CpG oligodeoxynucleotide is derived from a bacterial lysate.

BRIEF DESCRIPTION OF THE SEVERAL VIEWS OF THE DRAWINGS

The following figures form part of the present specification and are included to further demonstrate certain aspects of the present invention. The invention may be better understood by reference to one or more of these figures in combination with the detailed description of specific embodiments presented herein.

FIG. 5 illustrates the results of the Human TLR/NLR Ligand screening.

FIG. 6 illustrates the results of the NF-κB Control Cell screening.

Figure 1:
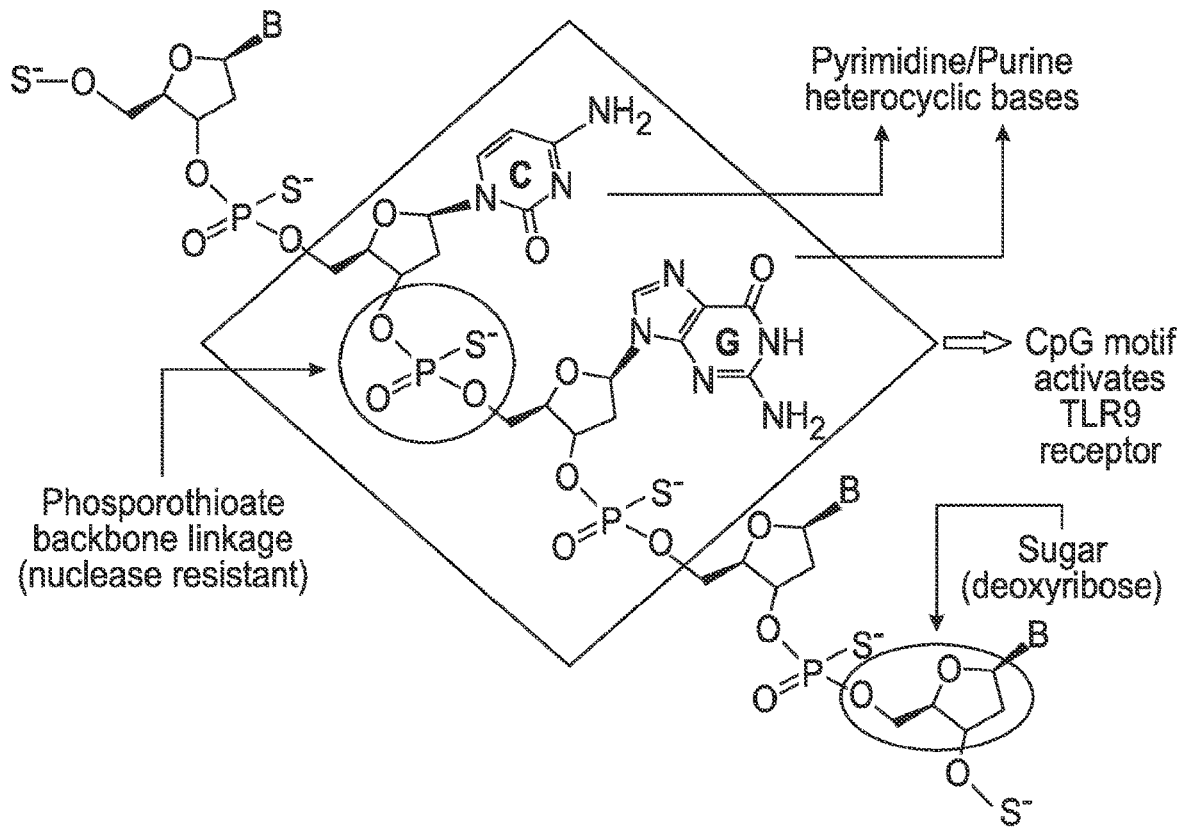
FIG. 1 illustrates an exemplary, generic structure of a CpG ODN suitable for use in accordance with the present disclosure.

While the inventions disclosed herein are susceptible to various modifications and alternative forms, only a few specific embodiments have been shown by way of example in the drawings and are described in detail below. The figures and detailed descriptions of these specific embodiments are not intended to limit the breadth or scope of the inventive concepts or the appended claims in any manner. Rather, the figures and detailed written descriptions are provided to illustrate the inventive concepts to a person of ordinary skill in the art and to enable such person to make and use the inventive concepts.

Definitions

The following definitions are provided in order to aid those skilled in the art in understanding the detailed description of the present invention. Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art.

The methods and techniques of the present invention are generally performed according to methods well known in the art and as described in various general and more specific references that are cited and discussed throughout the present specification unless otherwise indicated. Such references include, e.g., Sambrook and Russell, Molecular Cloning, A Laboratory Approach, Cold Spring Harbor Press, Cold Spring Harbor, N.Y. (2001), Ausubel, et al., Current Protocols in Molecular Biology, John Wiley & Sons, NY (2002), and Harlow and Lane Antibodies: A Laboratory Manual, Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As used herein, the term "CpG motif" means a nucleotide sequence which contains unmethylated cytosine-guanine dinucleotides (that is, a cytosine (C) followed by a guanine (G)) linked by a phosphate bond, or a phosphodiester backbone. These motifs are also referred to equivalently as "unmethylated cytosine-phosphate-guanine dinucleotide") and activates a biological response, such as an immune response.

As used herein, the term "CpG oligodeoxynucleotide" (referred to as "CpG ODN" hereafter) means an oligodeoxynucleotide (ODN) comprising at least two of the above CpG motifs. Such CpG ODN's may be class-A (Type D), class-B (Type K), class-C, class P, or class S, as appropriate.

Figure 2:
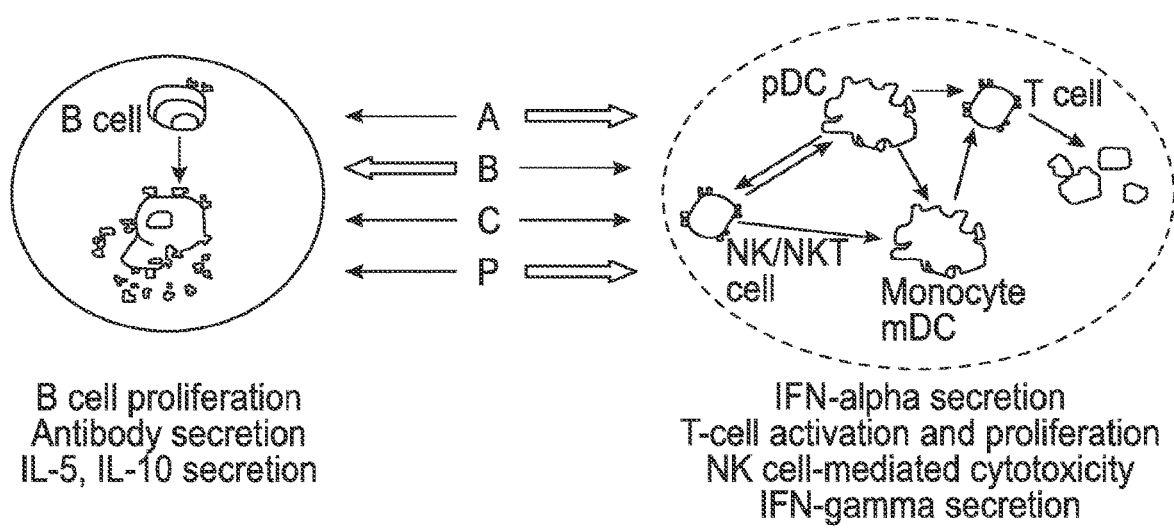
FIG. 2 illustrates various CpG motifs and their effects on the innate and adaptive immune systems.

In particular, several different classes of CpG oligonucleotides have recently been described. One class contains poly G motifs at one or both ends, and has been termed the A-class. One class is potent for activating B cells but is relatively weak in inducing IFN-α and NK cell activation; this class has been termed the B class. The B class CpG oligonucleotides are typically fully stabilized and include an unmethylated CpG dinucleotide within certain preferred base contexts. See, e.g., U.S. Pat. Nos. 6,194,388; 6,207,646; 6,214,806; 6,218,371; 6,239,116; and 6,339,068. Another class of CpG oligonucleotides activates B cells and NK cells and induces IFN-α; this class has been termed the C-class. The C-class CpG oligonucleotides, as first characterized, are typically fully stabilized; they include a B class-type sequence and a GC-rich palindrome or near-palindrome. This class has been described in International Patent Publication Number WO 03/015711. The A-Class oligonucleotides can form very complex higher ordered structures such as nanoparticles [Kerkmann, et al., J Biol. Chem. 280(9):8086-93 (2005)], and the C-Class may form intermolecular duplexes or hairpins. Recently, a new subclass of CpG oligonucleotides, that contain duplex forming regions such as, for example, perfect or imperfect palindromes at or near both the 5' and 3' ends, giving them the potential to form concatamers, have been described; see, e.g., U.S. Patent Publication No. 2008/0045473A1. These oligonucleotides referred to as P-Class oligonucleotides have the ability in some instances to induce much high levels of IFN-α secretion than the C-Class. The P-Class oligonucleotides have the ability to spontaneously self-assemble into concatamers either in vitro and/or in vivo. FIG. 2 (taken from Vollmer, J., et al., Advanced Drug Delivery Reviews, Vol. 61(3), pp. 195-204 (2009)) illustrates various CpG motifs and their effects on the innate and adaptive immune systems.

The phrase "pharmaceutical composition" refers to a formulation of a compound and a medium generally accepted in the art for the delivery of the biologically active compound to mammals, e.g., humans. Such a medium includes all pharmaceutically acceptable carriers, diluents or excipients therefore.

The phrase "pharmaceutically acceptable carrier, diluent or excipient" as used herein includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

By the term "effective amount", or "therapeutically effective amount," as used herein, is meant an amount that when administered to a mammal, preferably a human, mediates a detectable therapeutic response compared to the response detected in the absence of the compound. A therapeutic response, such as, but not limited to, increased overall survival, inhibition of and/or decreased tumor growth (including tumor size stasis), tumor size, metastasis, and the like, can be readily assessed by a plethora of art-recognized methods, including, e.g., such methods as disclosed herein.

The skilled artisan would understand that the effective amount of the CpG ODN, compound or composition administered herein varies and can be readily determined based on a number of factors such as the disease or condition being treated, the stage of the disease, the age and health and physical condition of the mammal being treated, the severity of the disease, the particular CpG ODN compound being administered, and the like.

The term "therapeutically effective amount", as used herein, the dose administered to an animal, such as a mammal, in particular a human, should be sufficient to prevent the targeted disease or disorder, e.g., cancer, delay its onset, slow its progression, or treat the disease or disorder (e.g., reverse or negate the condition). One skilled in the art will recognize that dosage will depend upon a variety of factors including the strength of the particular composition employed, as well as the age, species, condition, and body weight of the animal. The size of the dose will also be determined by the route, timing, and frequency of administration as well as the existence, nature, and extent of any adverse side-effects that might accompany the administration of a particular composition and the desired physiological effect.

"Biological active agent", as used herein, refers to any amino acid, peptide, protein, or antibody (including chimeric, monoclonal, isolated, or humanized antibodies), natural or synthetic, which exhibits a therapeutically useful effect. Such biologically active agents may include recombinant proteins, enzymes, peptoids, or PNAs, as well as combinations of such agents.

The phrase "pharmaceutically acceptable" or "pharmacologically-acceptable" refers to compositions that do not produce an allergic or similar unexpected reaction when administered to a human or animal in a medical or veterinary setting.

As used herein, to "prevent" means inhibiting the onset or development of symptoms of a disease (i.e., tumor growth and/or metastasis, or other effect mediated by the numbers and/or activity of immune cells, and the like) experienced by a patient. The term includes the administration of the CpG ODN, compounds or agents of the present invention to inhibit or delay the onset of the symptoms, complications, or biochemical indicia of a disease (e.g., elevation of PSA level in prostate cancer).

The term "ligand" as used herein means a molecular group that is associated with a central metal atom. The terms bidentate (or didentate), tridentate, tetradentate, and multidentate are used to indicate the number of potential binding sites of the ligand. For example, a carboxylic acid can be a bidentate or other multidentate ligand because it has at least two binding sites, the carboxyloxygen and hydroxyloxygen. In like manner, an amide has at least two binding sites, the carboxyloxygen and the nitrogen atom. An amino sugar can have at least two binding sites and many amino sugars will have multiple binding sites including the amino nitrogen, a hydroxyloxygen, an ethereal oxygen, an aldehyde carbonyl, and/or a ketone carbonyl.

The term "amino sugar" as used herein refers to monosaccharides having one alcoholic hydroxyl group (commonly but not necessarily in the '2-position') replaced by an amino group, systematically known as x-deoxy-x-monosaccharides. By way of non-limiting example, D-glucosamine or 2-amino-2-deoxy-D-glucopyranose is an amino sugar. Other illustrative amino sugars include but are not limited to erythrosamine, threosamine, ribosamine, arabinosamine, xylosamine, lyxosamine, allosamine, altrosamine, glucosamine, mannosamine, idosamine, galactosamine, talosamine, and their derivatives, all of which are suitable for use within the compositions of the present disclosure. The amino sugars include both aldose and ketose sugars. Additionally, the amino sugars may be of a straight-chain structure; however, the aldehyde or ketone group of the amino sugar may react with a hydroxyl group on a different carbon atom to form a hemiacetal or hemiketal, in which case there is an oxygen bridge between the two carbon atoms, forming a heterocyclic ring. Amino sugar rings with five and six atoms are called furanose and pyranose forms, respectively and exist in equilibrium with their corresponding straight-chain form. It should be noted that the ring form has one more optically active carbon than the straight-chain form, and so has both an $\alpha$- and a $\beta$-form, which interconvert in equilibrium. The term "amino sugar" also means glycosylamines, amino sugars where the nitrogen is substituted with a functional group other than H. Illustrative, non-limiting examples of glycosylamines include N-acetylglucosamine (NAG) and N-methylglucosamine.

The term "glycosaminoglycans" as used herein means any of any of a group of polysaccharides that contain amino sugars. Glycosaminoglycans can also form complexes with proteins.

The terms "hydrate" or "n-hydrate" as used herein means a molecular entity with some degree of hydration, where n is an integer representing the number of waters of hydration, e.g., monohydrate, dihydrate, trihydrate, tetrahydrate, pentahydrate, hexahydrate, septahydrate, octahydrate, nonahydrate, etc.

The compositions of the present invention may be prepared for pharmaceutical administration by methods and with excipients generally known in the art, such as described in *Remington's Pharmaceutical Sciences* [Troy, David B., Ed.; Lippincott, Williams and Wilkins; 21st Edition, (2005)].

"Treating" or "treatment" as used herein covers the treatment of the disease or condition of interest, e.g., tissue injury, in a mammal, preferably a human, having the disease or condition of interest, as well as prophylactic, or suppressive measures for the disease or disorder and includes: (i) preventing the disease or condition from occurring in a mammal, in particular, when such mammal is predisposed to the condition but has not yet been diagnosed as having it; (ii) inhibiting the disease or condition, i.e., arresting its development; (iii) relieving the disease or condition, i.e., causing regression of the disease or condition; or (iv) relieving the symptoms resulting from the disease or condition. Thus, for example, the term "treatment" includes the administration of an agent prior to or following the onset of a disease or disorder, thereby preventing or removing all signs of the disease or disorder. As another example, administration of the agent after clinical manifestation of the disease to combat the symptoms of the disease comprises "treatment" of the disease. Further, administration of the agent after onset and after clinical symptoms have developed where administration affects clinical parameters of the disease or disorder, such as the degree of tissue injury or the amelioration of the disease, comprises "treatment" of the disease.

The phrase "in need of treatment" includes mammals, such as humans, or animals, already having the disease or disorder, including those in which the disease or disorder is to be prevented.

As used herein, the terms "disease," "disorder," and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

As used herein, the expressions "agent", "composition", and "antagonist" are used interchangeably within the scope of the present disclosure, and are meant to include any molecule or substance which results in a therapeutic effect when administered to a subject suffering from a lymphatic disorder.

The term "iatrogenic disorder", as used herein, refers to those disorders induced by exposure to a therapeutic compound intended to treat some other disorder. Examples of drug induced liver diseases or disorders include, for example, chronic active hepatitis associated with the administration of Amineptine, Clometacine, Dantrolene, Diclofenac, and Fenofibrate to name a few; chronic cholestasis associated with the administration of Aceprometazine, Ajmaline and related drugs, Amitryptyline, and Ampicillin to name but a few; or hepatic granulomas associated with the administration of Allopurinal, Aspirin, and Diazepam. In this context, reference can be made to Tables 14.8, 14.10 and 14.11 of "MacSween's Pathology of the Liver, 5th Ed." [(Burt, Portman, and Ferrell, Eds.), Churchill Livingstone (2007), in Ch. 14, "Hepatic Injury Due to Drugs, Chemicals and Toxins" by Lewis, J. H. and Kleiner, D. E., pp. 649-759], the disclosure of which is incorporated in relevant part herein by reference.

The term "water-insoluble" encompasses the terms sparingly water-soluble, slightly or very slightly water-soluble, as well as practically or totally water-insoluble compounds [see, *Remington: The Science and Practice of Pharmacy*, vol. I, 194-195 (Gennaro, Ed., 1995)]. As used herein, a compound is water-insoluble for the purposes of this invention if it requires at least 30 parts solvent (e.g., water or saline) to dissolve one part solute (Id.). In accordance with the present disclosure, the term "water-insoluble" also encompasses oil- or lipid-soluble, as well as substantially oil- or lipid soluble.

Except as otherwise specifically provided or clear from the context, the term "compounds" of the invention should be construed as including the "pharmaceutically acceptable salts" thereof as appropriate (which expression has been eliminated in certain instances for the sake of brevity).

As used herein, the term "%" when used without qualification (as with w/v, v/v, or w/w) means % weight-involume for solutions of solids in liquids (w/v), % weight-in-volume for solutions of gases in liquids (w/v), % volume-in-volume for solutions of liquids in liquids (v/v) and weight-in-weight for mixtures of solids and semisolids (w/w), such as described in *Remington's Pharmaceutical Sciences* [Troy, David B., Ed.; Lippincott, Williams and Wilkins; 21st Edition, (2005)].

The terms "patient" and "subject", as used herein, are used interchangeably and refer generally to a mammal, and more particularly to human, ape, monkey, rat, pig, dog, rabbit, cat, cow, horse, mouse, sheep and goat. In accordance with this definition, lung surfaces or membranes described and referenced in accordance with this disclosure refer to those of a mammal, preferably a human or an animal test subject.

As used herein, "enhancing" and/or "providing relief" with respect to the therapeutic compositions disclosed, means that the administration of the referenced composition to a subject provides an immediate and/or extended alleviation, amelioration, inhibition, or mitigation of one or more symptoms of a hepatitis disorder to the subject mammal.

The term "drug" as used in conjunction with the present disclosure means any compound which is biologically active, e.g., exhibits or is capable of exhibiting a therapeutic or prophylactic effect in vivo, or a biological effect in vitro.

The term "dietary supplement, as used herein, refers to a compound or composition of either natural or synthetic origin which comprises a dietary or nutritional substance for use by people to supplement the diet by increasing the total dietary intake. In various embodiments, a dietary supplement may be a dietary supplement as defined under the Dietary Supplement Health and Education Act of 1994 (DSHEA), or the equivalent. The DSHEA requires that the dietary supplement is as a product that is intended to supplement the diet and contains at least one of the following: a vitamin, a mineral, an herb or other botanical (excluding tobacco), an amino acid, a dietary substance for use by people to supplement the diet by increasing the total dietary intake, or a concentrate, metabolite, constituent, extract, or combination of any of the above. Furthermore, DSHEA requires that the dietary supplement must also be intended for ingestion in pill, capsule, tablet, powder, liquid or other suitable oral form, not be represented for use as a conventional food or as the sole item of a meal or diet, and must be labeled as a "dietary supplement."

As used herein, the term "oral mucosa" refers to the mucous matrix that covers all structures inside the oral cavity except the teeth. The oral mucosa generally varies in color from pink to brownish purple depending on an individual's skin color. The structure of the oral mucosa varies depending on its location in the oral cavity and the function of that area. For example, the mucosa lining the cheeks is not designed to withstand the heavy force of mastication while the masticatory mucosa covering the jaws is structured to withstand the forces of mastication. A specialized mucosa that includes taste buds covers the tongue. Example of oral mucosa tissue include, but are not limited to, palate tissue, gingiva tissue, buccal mucosa tissue, tongue tissue, and floor of the mouth tissue.

The term "controlled drug-delivery system", or "DDS", as used herein, refers to a formulation that controls the rate and period of therapeutic agent/drug delivery (i.e., time-release dosage), targets specific areas of the subjects body, and are designed to maintain therapeutic levels during the desired treatment period, such as described by M. Vallet-Regi [*Chem. Eur. J.*, Vol. 12, pp. 5934-5943 (2006)].

The term "bioavailability" refers to the rate and/or extent to which a drug is absorbed or becomes available to the treatment site in the body.

The term "administering" as used herein refers to administration of the compositions of the present invention to the mucous membranes of the oral cavity (i.e., oral mucosa). Examples of suitable sites of administration within the oral mucosa include, without limitation, the mucous membranes of the floor of the mouth (sublingual mucosa), the cheeks (buccal mucosa), the gums (gingival mucosa), the roof of the mouth (palatal mucosa), the lining of the lips, and combinations thereof. Preferably, the compositions of the present invention are administered to the sublingual mucosa, buccal mucosa, or a combination thereof.

The term "functionally equivalent variants" as used herein refers to microorganisms which essentially have the same properties and functions as the original microorganisms. Such variants can be formed arbitrarily, for example, by UV irradiation, or other mutagenesis techniques known to a person skilled in the art, as well as taxonomical name changes, such as a change in the *Bifidobacteria* genus.

As used herein, the phrase "combination therapy" embraces the administration of a naturally-occurring immunostimulatory ODN, e.g., CpG ODN, and a chemotherapeutic agent as part of a specific treatment regimen optionally including a maintenance phase, intended to provide a beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" generally is not intended to encompass the administration of two or more of these therapeutic agents as part of separate monotherapy regimens that incidentally and arbitrarily result in the combinations of the present invention.

"Combination therapy" embraces administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular, subcutaneous routes, and direct absorption through mucous membrane tissues. The therapeutic agents can be administered by the same route or by different routes. For example, a first therapeutic agent (e.g., CpG ODN) can be administered by subcutaneous injection, and a second agent (e.g., a chemotherapeutic agent) can be administered intravenously. Further, a first therapeutic agent of the combination selected may be administered by intravenous injection while the other therapeutic agents of the combination may be administered orally. Alternatively, for example, both the therapeutic agents may be administered orally or both therapeutic agents may be administered by intravenous or subcutaneous injection.

In the present specification the term "sequential" means, unless otherwise specified, characterized by a regular sequence or order, e.g., if a dosage regimen includes the administration of a CpG ODN and a chemotherapeutic agent, a sequential dosage regimen could include administration of the CpG ODN before, simultaneously, substantially simultaneously, or after administration of the chemotherapeutic agent, but both agents will be administered in a regular sequence or order. The term "separate" means, unless otherwise specified, to keep apart one from the other. The term "simultaneously" means, unless otherwise specified, happening or done at the same time, i.e., the compounds of the invention are administered at the same time. The term "substantially simultaneously" means that the compounds are administered within minutes of each other (e.g., within 10 minutes of each other) and intends to embrace joint administration as well as consecutive administration, but if the administration is consecutive it is separated in time for only a short period (e.g., the time it would take a medical practitioner to administer two compounds separately). As used herein, concurrent administration and substantially simultaneous administration are used interchangeably. Sequential administration refers to temporally separated administration of the ODN and the chemotherapeutic agent.

"Combination therapy" also can embrace the administration of the therapeutic agents as described above in further combination with other biologically active ingredients (such as, but not limited to, a second and different antineoplastic agent, a dendritic vaccine or other tumor vaccine) and non-drug therapies (such as, but not limited to, surgery or radiation treatment or both). Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks. Such combination therapy may also alleviate one or more adverse or undesirable side effects of other therapeutic agents.

As used herein, the term "adjuvant therapy" refers to treatment given after the primary treatment, including, without limitation, radiation, chemotherapy, hormone therapy, etc. The goal of adjuvant therapy is to increase the patients' chances of remission or cure, to increase the patients' overall survival benefit, and to help decrease the risk of recurrence. Therefore, it will be understood that if the natural CpG ODN of the present disclosure is administered as an adjuvant, it will be administered to the patient after the primary treatment, e.g., the patient is given a regimen of chemotherapy, followed by a course of natural CpG ODN. In this regard, the dose of CpG ODN may be considered a therapeutic dose or a maintenance dose, depending on the goals of the adjuvant therapy. The term "neoadjuvant therapy" refers to treatment given before the primary treatment, including, without limitation, chemotherapy. In the neoadjuvant setting, the dose of CpG ODN is a therapeutic dose.

The term "first-line therapy" refers to the first type of therapy given for a condition or disease, or the first therapy of choice for the treatment of a particular type of cancer. It necessarily follows that the term "second-line therapy" therefore refers to the treatment given when the initial or first-line therapy is unsuccessful, and "third-line therapy" refers to a treatment or treatment regimen that is given when both the initial treatment and the subsequent treatment are unsuccessful.

As used herein, the term "lysing," with reference to a cell suspension, refers to rupturing the cell walls and/or cell membranes, cellular components, organelles of at least a portion of the cells such that at least part of the contents, e.g. biological molecules of the cells are released. In certain embodiments of the method of the present invention, at least a portion of the biological material is lysed to form a lysate. Without being bound by any particular theory of operation, the biological sample lyses under physico-chemical forces created by the combination of the appropriate solvent environment, along with pressure and either heat or cavitation, or a combination of the two. Biological molecules that are released upon lysing include, but are not limited to, nucleic acids, carbohydrates, amino acids, proteins, peptides, DNA (ssDNA, dsDNA and msDNA (multi-copy single-stranded DNA)), RNA (including ssRNA), complex sugars (oligosaccharides), peptidoglycans, and combinations thereof. Biological samples are typically aqueous, which means they contain an effective amount of water molecules to cause them to be in the liquid state.

The term "lysis" as used herein refers to the rupturing of a cell membrane or cell wall (e.g., by digestion using enzymes or other appropriate materials) and release of the cytoplasm from the cell. As used herein, the term "lysate" refers to the material produced by the destructive process of lysis, specifically a liquefied phase with lysed cell debris (e.g., ruptured cell walls and/or cell membranes) and DNA.

As used herein, the term "lysate" refers to the products of lysing biological material, for example, the biological molecules that are released as listed above. Although most lysates will be readily soluble in the biological sample fluid, certain lysate portions, such as hydrophobic components, may require additional steps to ensure at least a portion of the lysate is solubilized. Examples of additional steps for ensuring solubilization of the lysates include a suitable surfactant (or dehydrant), such as sodium dodecyl sulfate (SDS), which is typically included in the buffer, or any combination thereof. Lysate solubilization may also be assisted using vigorous mixing, shearing, heating in surfactant, cavitation, bead beating, boiling, degassing, or any combination thereof.

The term "cell", as used herein, is intended to encompass prokaryotic cells, eukaryotic cells, phage particles, and organelles.

As used herein, the term "chemotherapeutic agent" means a cytotoxic compound which inhibits the proliferation of tumor or cancers cells in a subject. Chemotherapeutic agents may, in some circumstances, have a cytotoxic effect on normal (non-cancerous and non-tumor) cells in a patient.

The term "downregulation" as used herein, refers to the process by which a cell decreases the quantity of a cellular component, such as RNA or a protein, in response to an external variable, such as a therapeutic agent.

The term "upregulation" as used herein refers to the process by which a cell increases the quantity of a cellular component, such as RNA or a protein, in response to an external variable, such as a therapeutic agent.

The term "Lyme disease," as used herein, refers to an disease which exhibits the characteristics as summarized in Dattwyler, R. J. and Wormser, G. "Lyme borreliosis." in *Infectious Diseases Medicine and Surgery* (eds.) S. Gorbach and J. Bartlett, 3rd Edition, Saunders Pub. New York, N.Y., 2003 and which is caused by a pathogenic *Borrelia*.

DETAILED DESCRIPTION

The Figures described above and the written description of specific structures and functions below are not presented to limit the scope of what Applicant has invented or the scope of the appended claims. Rather, the Figures and written description are provided to teach any person skilled in the art to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present inventions will require numerous implementation-specific decisions to achieve the developer's ultimate goal for the commercial embodiment. Such implementation-specific decisions may include, and likely are not limited to, compliance with system-related, business-related, government-related and other constraints, which may vary by specific implementation, location and from time to time. While a developer's efforts might be complex and time-consuming in an absolute sense, such efforts would be, nevertheless, a routine undertaking for those of skill in this art having benefit of this disclosure. It must be understood that the inventions disclosed and taught herein are susceptible to numerous and various modifications and alternative forms. Lastly, the use of a singular term, such as, but not limited to, "a," is not intended as limiting the number of items. Also, the use of relational terms, such as, but not limited to, "top," "bottom," "left," "right," "upper," "lower," "down," "up," "side," and the like are used in the written description for clarity in specific reference to the Figures and are not intended to limit the scope of the invention or the appended claims.

Applicant has created combination therapies and treatment regimens for the treatment of immune disorders, including, hepatic disorders and human immunodeficiency virus (HIV), cancers, and Lyme disease using a therapeutic agent derived from one or more gram-positive bacteria (such as a cell-wall fraction of a gram-positive bacteria), and a naturally-occurring immunostimulatory oligodeoxynucleotide. Exemplary immune disorders which may be treated by the compositions of the present disclosure, and using the associated methods, includes T lymphocyte-related disorders, including, but not limited to, chronic inflammatory diseases and disorders, such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis) and certain viral infections, including HIV, and bacterial infections, including tuberculosis and lepromatous leprosy.

A. Compositions.

The therapeutically active compositions of the present disclosure include a first biologically active agent, preferably one or more cell wall fractions of one or more gram positive bacteria, such as in the form of a lysate; a second biologically-active agent, preferably a naturally-occurring CpG ODN; an optional promoter; and optionally, one or more other additives, including control-release ingredients, so as to allow the composition to be absorbed into, or interact with, a mucosal wall of the subject in need of therapy.

According to the present invention, the first biologically active therapeutic agent is a mixture of one or more lysate or cell wall fraction of a gram-positive bacteria, in an amount ranging from about 1 mg/kg to about 100 mg/kg, as required depending upon the specific therapeutic application. In accordance with the present disclosure, the lysate or cell wall fraction of a gram-positive bacteria is from the group of gram-positive bacteria selected from the group consisting of *Lactobacillus acidophilus*, *Lactobacillus buchneri*, *Lactobacillus casei*, *Lactobacillus catenaforme*, *Lactobacillus cellobiosus*, *Lactobacillus crispatus*, *Lactobacillus curvatus*, *Lactobacillus delbrueckii*, *Lactobacillus delbrueckii* subsp. *bulgaricus*, *Lactobacillus delbrueckii* subsp. *lactis*, *Lactobacillus helveticus*, *Lactobacillus jensenii*, *Lactobacillus leichmannii*, *Lactobacillus minutus*, *Lactobacillus para casei*, *Lactobacillus plantarum*, *Lactobacillus rhamnosus*, *Lactobacillus rogosae*, *Lactobacillus salivarius*, *Lactobacillus sporogenes* (also known as *Bacillus coagulans*), *Lactobacillus brevis*, *Lactobacillus gasseri*, *Lactobacillus fermentum*, *Bifidobacterium adolescentis*, *Bifidobacterium animalis* (especially *B. animalis*, subspecies *animalis*), *Bifidobacterium angulatum*, *Bifidobacterium bifidum*, *Bifidobacterium breve*, *Bifidobacterium catenulatum*, *Bifidobacterium dentium*, *Bifidobacterium eriksonii*, *Bifidobacterium infantis*, *Bifidobacterium lactis* (*Bifidobacterium animalis* subsp. *lactis*), *Bifidobacterium longum*, *Bifidobacterium plantarum*, *Bifidobacterium pseudocatenulatum*, *Bifidobacterium pseudo-longum*, *Leptococcus lactis*, *Streptococcus lactis* (also referred to as *Lactococcus lactis* subsp. *lactis*), *Streptococcus raffinolactis*, *Acidaminococcus fermenta*, *Cytophaga fermentans*, *Rhodoferax fermentans*, *Cellulomonas fermentans*, *Zymomonas mobilis*, and *Streptococcus thermophilus*, as well as functionally equivalent variants thereof, all of which are suitable for carrying out the present invention. These mixtures of well-known species can be easily prepared by any person having ordinary experience in this field.

Other species can be used, for example those disclosed in the state of the art and generally available in collections, such as the ECACC (European Collection of Cell Cultures), ASTM; and DSM.

The preferred first biologically therapeutic active agents according to the present invention are lysates or cell wall extracts of gram-positive bacteria selected from the group consisting of the following: *Streptococcus thermophilus*, *Bifidobacterium animalis* (especially *B. animalis*, subspecies *animalis*), *Bifidobacterium infantis*, *Bifidobacterium longum*, *Bifidobacterium breve*, *Lactobacillus acidophilus*, *Lactobacillus plantarum*, *Lactobacillus casei*, *Lactobacillus delbrueckii* subsp. *bulgaricus*, *Lactococcus lactis*, *Bacillus coagulans* (*Lactobacillus sporogenes*), *Bifidobacterium lactis* (*Bifidobacterium animalis* subsp. *lactis*), *Bifidobacterium breve*, *Lactobacillus acidophilus*, *Lactobacillus plantarum*, *Lactobacillus casei*, *Lactobacillus rhamnosus*, and *Lactobacillus helveticus*, as well as functionally equivalent variants thereof. Some of these mixtures are commercially available in a lyophilized form.

The second biologically-active therapeutic agent is a naturally-occurring CpG ODN. It is preferred, but not necessary, that the naturally-occurring CpG ODN be obtained from the same bacteria or bacterial lysate from which the first biologically-active therapeutic agent is obtained. The CpG ODN may be any CpG motif, including but not limited to, class-A (Type D), class-B (Type K), class-C, class P, or class S, or combinations thereof, as appropriate. The second biologically-active therapeutic agent may be a single CpG ODN, or a combination of two or more CpG ODN's, including a combination of naturally-occurring and synthetic CpG ODN's, the only proviso being that at least one of the two or more CpG ODN's be naturally-occurring. The present invention further contemplates the administration of a therapeutic or both therapeutic and maintenance dose of the CpG ODN component in a wide range of doses. Exemplary therapeutic and/or maintenance doses of the CpG ODN component of the instant composition includes, but are not limited to, dose ranges of from about 0.001 mg/kg to about 5.0 mg/kg, preferably about 0.001 mg/kg to about 2.5 mg/kg, from one to up to three times per day. The present invention contemplates, in addition to a therapeutic dose, the administration of a maintenance dose of a CpG ODN of about 0.001 to about 5.0 mg/Kg, as part of a maintenance regimen, such CpG ODN used as a maintenance does being either the same or not the same as the CpG ODN within the lysate of the gram-positive bacteria, as appropriate.

The therapeutic compositions of the present disclosure may further and optionally comprise one or more promoters, to assist in the therapeutic delivery of the active agent across the biological membrane. Preferably, the promoter useful in accordance with the present disclosure is an amino acid, N-alkylated peptide, sugar, amino sugar or amino sugar chelate. An amino sugar chelate comprising one or more amino sugar ligands, one or more saturated hydroxylated carboxylic acid ligands, and a nutritionally acceptable metal, wherein at least one of the one or more amino sugar ligands is glucosamine, and wherein the metal is selected from the group consisting of manganese, magnesium, sodium, potassium, and zinc, and wherein the one or more saturated hydroxylated carboxylic acid ligands is gluconic acid, and wherein the glucosamine ligand to nutritionally acceptable metal ratio is 2:1.

In accordance with one aspect of the present disclosure, the therapeutic formulations may include one or more acetylated or deacetylated amino sugars selected from the group consisting of N-acetylglucosamine (NAG; GlcNAc), galactosamine, N-acetylgalactosamine, mannosamine, N-acetyl cysteine (NAC) and N-acetylmannosamine in the form of monomers, oligomers, and/or polymers thereof including chitin, and human glucosaminoglycans, as well as derivatives thereof. The term "derivatives thereof" used herein with reference to amino sugars means derivatives of the amino sugars having the same or essentially the same ability to form cytotoxic degradation products during sterilization. In accordance with select further aspects of the present disclosure, the promoter is a member selected from the group consisting of poly-L-lysine, glucosamine, poly-L-arginine, galactosamine, N-acetylmannosamine (NAM; N—Ac-Man), N-acetylglucosamine (NAG; N—Ac-Glc), N,N'-diacetylglucosamine (NAG-NAG; N,N'-diacetylchitobiose), N,N',N'',N'''-tetraacetylglucosamine (NAG-NAG-NAG-NAG; N,N',N'',N'''-tetraacetylchitotetraose), and mixtures thereof.

Optionally, and equally acceptable, the promoter may be an acylated glycosyloxy sugar or an optionally acylated oligoglycosyloxy sugar moiety of 2 to 12 α-1,2 and/or α-1,6 linked sugars, wherein the sugar(s) are selected from the group consisting of D-mannose, D-galactose, D-glucose, D-glucosamine, N-acetylglucosamine, and 6-deoxy-L-mannose, wherein an oligoglycosyloxy sugar moiety may comprise the same or different sugars.

In accordance with further aspects of the present disclosure, the therapeutic formulations of the invention may further comprise one or more additional therapeutic agents, such as the second therapeutic agents described below. The compositions will usually be supplied as part of a sterile, pharmaceutical composition that will normally include a pharmaceutically acceptable carrier. This composition, comprising additional therapeutic agents, can be in any suitable form (depending upon the desired method of administering it to a patient).

In certain aspects, the second therapeutic agent is an anti-rheumatic drug, an anti-inflammatory agent, a chemotherapeutic agent, a radiotherapeutic, an immunosuppressive agent, an interferon, an interferon-based chemotherapeutic, a different bacterial wall lysate, or a cytotoxic drug.

Anti-rheumatic drugs include, but are not limited to, auranofin, azathioprine, chloroquine, D-penicillamine, gold sodium thiomalate hydroxychloroquine, Myocrisin and sulfasalazine methotrexate.

Anti-inflammatory agents include, but are not limited to, dexamethasone, pentasa, mesalazine, asacol, codeine phosphate, benorylate, fenbufen, naprosyn, diclofenac, etodolac and indomethacin, aspirin and ibuprofen, as well as non-steroidal anti-inflammatory agents (NSAIDS).

Chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. Examples of suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC)), anti-mitotic agents, cis-dichlorodiamine platinum (II) (DDP) cisplatin), diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucovorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, E. coli L-asparaginase, emetine, epoetin-.alpha., Erwinia L-asparaginase, esterified estrogens, estradiol, estramustine phosphate sodium, ethidium bromide, ethinyl estradiol, etidronate, etoposide citrovorum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon .alpha.-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptopurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

In yet other aspects of the disclosure, the second therapeutic agent is a TNF-α antagonist or an anti-TNF-α antibody of the disclosure. Examples of such TNF-α antagonists include, but are not limited to, soluble TNF-α receptors; etanercept (ENBREL®; Immunex) or a fragment, derivative or analog thereof; infliximab (REMICADE®; Centacor) or a derivative, analog or antigen-binding fragment thereof; IL-10, which is known to block TNF-α production via interferon-γ-activated macrophages, TNFR-IgG; the murine product TBP-1; the vaccine CytoTAb (Protherics); antisense molecule 104838 (ISIS); the peptide RDP-58 (SangStat); thalidomide (Celgene); CDC-801 (Celgene); DPC-333 (Dupont); VX-745 (Vertex); AGIX-4207 (AtheroGenics); ITF-2357 (Italfarmaco); NPI-13021-31 (Nereus); SCIO-469 (Scios); TACE targeter (Immunix/AHP); CLX-120500 (Calyx); Thiazolopyrim (Dynavax); auranofin (Ridaura) (SmithKline Beecham Pharmaceuticals); quinacrine (mepacrine dichlorohydrate); tenidap (Enablex); Melanin (Large Scale Biological); and anti-p38 MAPK agents by Uriach.

Additionally, the second therapeutic agents may be made from particulate cellular wall fragments of particular lactic acid bacteria (e.g., Del-Immune V®, Pure Research Products, LLC, Colorado, USA), which are intended to stimulate the immune system.

In another embodiment, the compositions of the present invention are in a dosage form selected from the group consisting of a lozenge, a chewing gum, a chewable tablet, and a dissolving tablet such as a slow-dissolving tablet, a quick-dissolving tablet, or a controlled-release tablet or other suitable controlled-release formulation. Preferably, the composition is a lozenge or a dissolving tablet.

In a preferred embodiment, the active agent of the present disclosure is delivered across an oral mucosa of a subject, the oral mucosa being selected from the group consisting of the sublingual mucosa, the buccal mucosa, and a combination thereof. Preferably, the composition is administered sublingually so that the active ingredient is delivered across the sublingual mucosa.

In another embodiment, the carrier is typically a solid, semi-solid, or liquid such as a binder, a gum base, or combinations thereof. Suitable binders for use in the compositions of the present invention include, without limitation, sugar alcohols such as mannitol, sorbitol, and xylitol; sugars such as lactose, dextrose, sucrose, glucose, and powdered sugar; other substances such as inositol, molasses, maltodextrin, starch, cellulose, microcrystalline cellulose, polyvinylpyrrolidone, acacia gum, guar gum, tragacanth gum, alginate, extract of Irish moss, panwar gum, ghatti gum, mucilage of isapol husks, VEEGUM®, larch arabogalactan, gelatin, methylcellulose, ethylcellulose, carboxymethylcellulose, hydroxypropylmethylcellulose, polyacrylic acid (e.g., Carbopol), calcium silicate, calcium phosphate, dicalcium phosphate, calcium sulfate, kaolin, sodium chloride, polyethylene glycol; and combinations thereof. Suitable gum bases for use in the compositions of the present invention include, for example, materials selected from among the many water-insoluble and saliva-insoluble gum base materials known in the art. In certain instances, the gum base comprises at least one hydrophobic polymer and at least one hydrophilic polymer. Non-limiting examples of suitable hydrophobic and hydrophilic polymers for gum bases include both natural and synthetic polymers such as elastomers, rubbers, and combinations thereof. Examples of suitable natural polymers include, without limitation, substances of plant origin such as chicle, jelutong, gutta percha, crown gum, and combinations thereof. Examples of suitable synthetic polymers include elastomers such as butadiene-styrene copolymers, isobutylene and isoprene copolymers (e.g., "butyl rubber"), polyethylene, polyisobutylene, polyvinylester (e.g., polyvinyl acetate and polyvinyl acetate phthalate), and combinations thereof. In other instances, the gum base comprises a mixture of butyl rubber (i.e., isobutylene and isoprene copolymer), polyisobutylene, and optionally, polyvinylacetate (e.g., having a molecular weight of approximately 12,000).

In yet another embodiment, the compositions of the present invention can further comprise a sweetening agent, a flavoring agent, a protecting agent, a plasticizer, a wax, an elastomeric solvent, a filler material, a preservative, or combinations thereof. In still yet another embodiment, the compositions of the present invention can further comprise a lubricating agent, a wetting agent, an emulsifying agent, a solubilizing agent, a suspending agent, a coloring agent, a disintegrating agent, or combinations thereof. In a preferred embodiment, the average particle size of the drug in the compositions described herein is about 20 microns, as compared to a typical average drug particle size of from about 75 to about 100 microns. In another preferred embodiment, the average particle size of the drug in the compositions described herein is less than or equal to the average particle size of the carrier ingredients (e.g., gum base, binders, etc.).

In one aspect of the present disclosure, the therapeutic composition may optionally include a buffer system to raise the pH of saliva to a pH of from about 8.0 to about 11, irrespective of the starting pH of saliva in the oral cavity of the subject to be treated. Suitable therapeutic agents for use in the present invention are described above. Suitable carbonate salts and bicarbonate salts for use in the buffer systems of the present invention are also described above. In certain instances, composition further comprises a non-biologic therapeutic agent, such as an NSAID.

Suitable citrate, phosphate, and borate salts include, without limitation, any salt of citric acid, phosphoric acid, or boric acid known in the art. For example, in some embodiments, the citrate salt is selected from the group consisting of sodium citrate, potassium citrate, calcium citrate, magnesium citrate, and ammonium citrate. In other embodiments, the phosphate salt is selected from the group consisting of monobasic sodium phosphate, dibasic sodium phosphate, monobasic potassium phosphate, dibasic potassium phosphate, monobasic calcium phosphate, dibasic calcium phosphate, monobasic magnesium phosphate, dibasic magnesium phosphate, monobasic ammonium phosphate, and dibasic ammonium phosphate. In yet other embodiments, the borate salt is selected from the group consisting of sodium borate, potassium borate, calcium borate, magnesium borate, and ammonium borate. In certain instances, the buffer system comprises a carbonate salt, a bicarbonate salt, and/or a citrate salt. In certain other instances, the buffer system comprises a carbonate salt, a bicarbonate salt, and/or a phosphate salt. In further instances, the buffer system comprises a carbonate salt, a bicarbonate salt, and/or a borate salt.

In addition to a buffer system comprising a carbonate salt, a bicarbonate salt, and/or a metal oxide, other buffer systems are suitable for use in the compositions of the present invention. For example, in an alternative embodiment, the ternary buffer system comprises a carbonate salt, a bicarbonate salt, and a citrate, phosphate, or borate salt. In another alternative embodiment, the buffer system comprises a carbonate salt or a bicarbonate salt and two or more buffering agents selected from the group consisting of a metal oxide, a citrate salt, a phosphate salt, and a borate salt. In yet another alternative embodiment, the buffer system is a binary buffer system comprising a carbonate salt or a bicarbonate salt and a metal oxide. In still yet another alternative embodiment, the buffer system is a binary buffer system comprising, a carbonate salt or a bicarbonate salt and a citrate, phosphate, or borate salt. In a further alternative embodiment, the buffer system is a binary buffer system comprising a metal oxide and a citrate, phosphate, or borate salt. In still yet another alternative embodiment, the buffer system is a binary buffer system comprising a carbonate salt and a bicarbonate salt, preferably sodium carbonate and sodium bicarbonate.

B. Control Release Additives

The therapeutic composition of the invention may also include a controlled release additive. The presence of a controlled release additive in the therapeutic composition substantially reduces the "initial burst" of biologically active agent released from the therapeutic composition during the initial first 1-2 minutes after delivery to the subject's mucosa. As used herein, the term "substantially reduces" means a decrease of at least 15% of biologically active agent released from the therapeutic composition compared to a composition without the additive. Preferably, the controlled release additive reduces the initial burst of biologically active agent released from the polymeric composition by about 15% to about 70%, more preferably about 30% to about 60%, compared to a therapeutic composition which does not include a controlled release additive.

According to the present disclosure, the controlled release additive is any suitable controlled-release additive, preferably a thermoplastic polymer having poly(lactide-co-glycolide) (PLG) moieties and polyethylene glycol (PEG) moieties. Preferably the controlled release additive is a PLG/PEG block copolymer which includes from about 50 mole % to about 90 mole % lactide monomers and about 50 mole % to about 10 mole % glycolide monomers. More preferably, the PLG/PEG block copolymer includes from about 50 mole % to about 75 mole % lactide monomers and about 50 mole % to about 25 mole % glycolide monomers. Preferably the PEG moiety has a molecular weight of about 1,000 Daltons to about 10,000 Daltons, more preferably about 5000 Daltons. The PEG portion of the block copolymer ranges from about 1 wt % to about 20 wt % of the total weight of the block copolymer. The percentage is dependent on the molecular weight of the block copolymer that is prepared and the molecular weight of the polyethylene glycol that is used. Thus, a block copolymer with a weight average molecular weight of 100,000 Daltons (I.V. approx. 0.8 dL/g) prepared with PEG having a molecular weight of 5,000 Daltons will contain about 5 wt % PEG. If PEG with a molecular weight of 1,000 Daltons is used, the block copolymer will include about 1 wt % of PEG.

The inherent viscosity (abbreviated as "I.V."; units are in deciliters/gram) of the controlled release additive is a measure of its molecular weight. Preferably, the inherent viscosity of the controlled release additive suitable for use with the compositions of the present disclosure is from about 0.50 dL/g to about 1.0 dL/g (as measured in chloroform), more preferably from about 0.70 dL/g to about 0.90 dL/g.

Suitable polymeric controlled release additives include but are not limited to any PLG/PEG block copolymer with the previously mentioned attributes. Examples of suitable polymeric controlled release additives include, without limitation, 50/50 PLG/PEG-5000 (0.81); 70/30 PLG/PEG-5000 (0.73); and 70/30 PLG/PEG-5000 (0.79).

The controlled release additive, when included in the formulation, may be present in the therapeutic composition in an amount effective to reduce the initial burst of biologically active agent released from the therapeutic composition during the first 2 minutes after delivery to the mucosa. Preferably, the therapeutic composition includes about 1 wt % to about 50 wt %, more preferably about 2 wt % to about 20 wt % of the controlled release additive.

C. Dosage Forms

The therapeutic compositions of the present invention may take the form of solid, semi-solid, lyophilized powder, or liquid dosage forms, such as, for example, tablets (e.g., chewable, slow-dissolving, quick-dissolving), pills, capsules, lozenges, candies, gums, powders, solutions, suspensions, emulsions, aerosols, or the like. Preferably, the dosage form is a chewing gum, quick-dissolving tablet, candy, or lozenge. In accordance with further aspects of the present disclosure, the composition is in a dietary supplement, such as a tablet, pill, capsule, or other oral delivery formulation.

While each subject or patient possesses unique factors that may affect the rate and extent of absorption of the therapeutic agents described herein, dosage forms such as chewing gums, candies, quick-dissolving tablets, or lozenges offer advantages over the traditional dosage forms for oral administration. For example, each of these dosage forms avoids hepatic first pass metabolism, degradation within the gastrointestinal tract, and drug loss during absorption. Consequently, the amount of the active therapeutic agent required per dose is less than that which would be required if formulated, for example, in a pill or tablet for oral administration. Similarly, with each of these dosage forms, the bioavailability of the therapeutic agent is increased, thereby reducing the time to onset of therapeutic activity.

As used herein, the term "dosage form" refers to physically discrete units suitable as unitary dosages for human subjects and other mammals, each unit containing a predetermined quantity of therapeutic agent calculated to produce the desired onset, tolerability, and therapeutic effects, in association with one or more suitable pharmaceutical excipients such as carriers. Methods for preparing such dosage forms are known or will be apparent to those skilled in the art. For example, in some embodiments, a chewing gum dosage form of the present invention can be prepared according to procedures standard in the industry. In other embodiments, a tablet, lozenge, or candy dosage form (e.g., a sucker) of the present invention can be prepared according to the procedures set forth in, for example, Remington's "The Science and Practice of Pharmacy, 20th Ed.," [Lippincott, Williams & Wilkins (2003); and, "Pharmaceutical Dosage Forms, Volume 1: Tablets," 2nd Ed., Marcel Dekker, Inc., New York, N.Y. (1989)]. The dosage form to be administered will, in any event, contain a quantity of the active therapeutic agent in a therapeutically effective amount for relief of the condition being treated when administered in accordance with the teachings of this invention.

As used herein, the term "carrier" refers to a typically inert substance used as a diluent or vehicle for a drug such as a therapeutic agent. The term also encompasses a typically inert substance that imparts cohesive qualities to the composition. Suitable carriers for use in the compositions of the present invention include, without limitation, a solid, semi-solid, or liquid such as a binder or a gum base. Non-limiting examples of binders include mannitol, sorbitol, xylitol, maltodextrin, lactose, dextrose, sucrose, glucose, inositol, powdered sugar, molasses, starch, cellulose, microcrystalline cellulose, polyvinylpyrrolidone, acacia gum, guar gum, tragacanth gum, alginate, extract of Irish moss, panwar gum, ghatti gum, mucilage of isapol husks, VEEGUM®, larch arabogalactan, gelatin, methylcellulose, ethylcellulose, carboxymethylcellulose, hydroxypropylmethylcellulose, polyacrylic acid (e.g., Carbopol), calcium silicate, calcium phosphate, dicalcium phosphate, calcium sulfate, kaolin, sodium chloride, polyethylene glycol, and combinations thereof. These binders can be pre-processed to improve their flowability and taste by methods known in the art such as freeze drying [see, e.g., "Fundamentals of Freeze-Drying," Pharm. Biotechnol., Vol. 14, pp. 281-360 (2002); "Lyophililization of Unit Dose Pharmaceutical Dosage Forms," Drug. Dev. Ind. Pharm., Vol. 29, pp. 595-602 (2003)]; solid-solution preparation; and lubricant dusting and wet-granulation preparation with a suitable lubricating agent (see, e.g., Remington: The Science and Practice of Pharmacy, supra). For example, MANNOGEM® and SORBOGEM®, sold by SPI Pharma Group (New Castle, Del.), are freeze-dried, processed forms of mannitol and sorbitol, respectively. Typically, when a binder is included in the formulation, the compositions of the present invention comprise from about 15% to about 90% by weight of the binder, and preferably from about 35% to about 80%. However, one skilled in the art will appreciate that the compositions of the present invention can be made without any binders, e.g., to produce a highly friable dosage form.

Non-limiting examples of gum bases include materials selected from among the many water-insoluble and saliva-insoluble gum base materials known in the art. For example, in some instances, the gum base comprises at least one hydrophobic polymer and at least one hydrophilic polymer. Non-limiting examples of suitable hydrophobic and hydrophilic polymers for gum bases include both natural and synthetic polymers such as elastomers, rubbers, and combinations thereof. Examples of suitable natural polymers include, without limitation, substances of plant origin such as chicle, jelutong, gutta percha, crown gum, and combinations thereof. Examples of suitable synthetic polymers include elastomers such as butadiene-styrene copolymers, isobutylene and isoprene copolymers (e.g., "butyl rubber"), polyethylene, polyisobutylene, polyvinylester (e.g., polyvinyl acetate and polyvinyl acetate phthalate), and combinations thereof. In other instances, the gum base comprises a mixture of butyl rubber (i.e., isobutylene and isoprene copolymer), polyisobutylene, and optionally, polyvinylacetate (e.g., having a molecular weight of approximately 12,000). Typically, the gum base comprises from about 25% to about 75% by weight of these polymers, and preferably from about 30% to about 60%.

The compositions of the present invention can additionally include lubricating agents; wetting agents; emulsifying agents; solubilizing agents; suspending agents; preserving agents such as methyl-, ethyl-, and propyl-hydroxy-benzoates, butylated hydroxytoluene, and butylated hydroxyanisole; sweetening agents; flavoring agents; coloring agents; lipids such as vitamin E or an omega fatty acid; and disintegrating agents (i.e., dissolving agents) such as crospovidone as well as croscarmellose sodium and other cross-linked cellulose polymers.

Lubricating agents can be used to prevent adhesion of the dosage form to the surface of the dies and punches, and to reduce inter-particle friction. Lubricating agents may also facilitate ejection of the dosage form from the die cavity and improve the rate of granulation flow during processing. Examples of suitable lubricating agents include, without limitation, magnesium stearate, calcium stearate, zinc stearate, stearic acid, simethicone, silicon dioxide, talc, hydrogenated vegetable oil, polyethylene glycol, mineral oil, and combinations thereof. The compositions of the present invention can comprise from about 0% to about 10% by weight of the lubricating agent, and preferably from about 1% to about 5%.

Sweetening agents can be used to improve the palatability of the composition by masking any unpleasant tastes it may have. Examples of suitable sweetening agents include, without limitation, compounds selected from the saccharide family such as the mono-, di-, tri-, poly-, and oligosaccharides; sugars such as sucrose, glucose (corn syrup), dextrose, invert sugar, fructose, maltodextrin, and polydextrose; saccharin and salts thereof such as sodium and calcium salts; cyclamic acid and salts thereof; dipeptide sweeteners; chlorinated sugar derivatives such as sucralose and dihydrochalcone; sugar alcohols such as sorbitol, sorbitol syrup, mannitol, xylitol, hexa-resorcinol, and the like, and combinations thereof. Hydrogenated starch hydrolysate, and the potassium, calcium, and sodium salts of 3,6-dihydro-6-methyl-1-1,2,3-oxathiazin-4-one-2,2-dioxide may also be used. Of the foregoing, sorbitol, mannitol, and xylitol, either alone or in combination, are preferred sweetening agents. The compositions of the present invention can comprise from about 0% to about 80% by weight of the sweetening agent, preferably from about 5% to about 75%, and more preferably from about 25% to about 50%.

Flavoring agents can also be used to improve the palatability of the composition. Examples of suitable flavoring agents include, without limitation, natural and/or synthetic (i.e., artificial) compounds such as peppermint, spearmint, wintergreen, cinnamon, menthol, cherry, strawberry, watermelon, grape, banana, peach, pineapple, apricot, pear, raspberry, lemon, grapefruit, orange, plum, apple, fruit punch, passion fruit, chocolate (e.g. white, milk, dark), vanilla, caramel, coffee, hazelnut, combinations thereof, and the like. Coloring agents can be used to color code the composition, for example, to indicate the type and dosage of the therapeutic agent therein. Suitable coloring agents include, without limitation, natural and/or artificial compounds such as FD & C coloring agents, natural juice concentrates, pigments such as titanium oxide, silicon dioxide, and zinc oxide, combinations thereof, and the like. The compositions of the present invention can comprise from about 0% to about 10% by weight of the flavoring and/or coloring agent, preferably from about 0.1% to about 5%, and more preferably from about 2% to about 3%.

1. Chewing Gums

When the dosage form is a chewing gum, the compositions of the present invention comprise an active therapeutic agent derived from a gram-positive bacteria or a pharmaceutically acceptable salt thereof, a promoter, a carrier such as a gum base, a binary or ternary buffer system, and optionally a protecting agent. The chewing gum composition may further comprise lubricating agents, wetting agents, emulsifying agents, suspending agents, preserving agents, sweetening agents, flavoring agents, and coloring agents. Typically, the chewing gum composition comprises from about 0.001% to about 10.0% by weight of the active therapeutic agent (in whatever chosen form, measured as per its free base form), more typically from about 0.01% to about 5.0%, and still more typically from about 0.1% to about 3.0%. One skilled in the art understands that the foregoing percentages will vary depending upon the particular source of gram-positive-based active therapeutic agent utilized, the amount of the active therapeutic agent desired in the final formulation, as well as on the particular release rate of the active therapeutic agent desired. The optional buffer system of the chewing gum composition can provide for a final salivary pH in excess of at least about 8.0, preferably at least about 9.5, and more preferably in the range of from about 9.9 to about 11. The chewing gum composition typically comprises from about 20% to about 95% by weight of the gum base, more typically from about 30% to about 85%, and most typically from about 50% to about 70% of the gum base.

The chewing gum composition may further comprise a protecting agent. The protecting agent coats at least part of the therapeutic agent, typically upon the mixing of the two agents. The protecting agent may be mixed with the active therapeutic agent in a ratio of from about 0.1 to about 100 by weight, preferably in a ratio of from about 1 to about 50, and more preferably in a ratio of about 1 to about 10. Without being bound to any particular theory, the protecting agent reduces the adhesion between the therapeutic agent and the gum base so that the therapeutic agent may be more easily released from the gum base. In this way, the therapeutic agent may be delivered across the mucous membranes of the oral cavity within about 5 to about 20 minutes of chewing, preferably within about 10 minutes of chewing. A variety of different protecting agents may be used. Examples of suitable protecting agents include, without limitation, calcium stearate, glycerin monostearate, glyceryl behenate, glyceryl palmitostearate, hydrogenated castor oil, hydrogenated vegetable oil type I, light mineral oil, magnesium lauryl sulfate, magnesium stearate, mineral oil, poloxamer, polyethylene gycol, sodium benzoate, sodium chloride, sodium lauryl sulfate, stearic acid, cab-o-sil, talc, zinc stearate, and combinations thereof.

The gum base may additionally include plasticizers such as softeners or emulsifiers. Such plasticizers may, for example, help reduce the viscosity of the gum base to a desirable consistency and improve its overall texture and bite. Plasticizers may also facilitate the release of the therapeutic agent upon mastication. Non-limiting examples of plasticizers include lecithin, mono- and diglycerides, lanolin, stearic acid, sodium stearate, potassium stearate, glycerol triacetate, glycerol monostearate, glycerin, and combinations thereof. The gum base typically comprises from about 0% to about 20% by weight of the plasticizer, and more typically from about 5% to about 15%.

The gum base may further comprise waxes such as beeswax and microcrystalline wax, fats or oils such as soybean and cottonseed oil, and combinations thereof. Typically, the gum base comprises from about 0% to about 25% by weight of these waxes and oils, and more typically comprises from about 15% to about 20%.

In addition, the gum base may further comprise one or more elastomeric solvents such as rosins and resins. Non-limiting examples of such solvents include methyl, glycerol, and pentaerythritol esters of rosins, modified rosins such as hydrogenated, dimerized or polymerized rosins, or combinations thereof (e.g., pentaerythritol ester of partially hydrogenated wood rosin, pentaerythritol ester of wood rosin, glycerol ester of wood rosin, glycerol ester of partially dimerized rosin, glycerol ester of polymerized rosin, glycerol ester of tall oil rosin, glycerol ester of wood rosin and partially hydrogenated wood rosin and partially hydrogenated methyl ester of rosin such as polymers of α-pinene or β-pinene, terpene resins including polyterpene, and combinations thereof). Typically, the gum base comprises from about 0% to about 75% by weight of the elastomeric solvent, and more typically less than about 10%.

The gum base may further comprise a filler material to enhance the chewability of the final chewing gum composition. Fillers that are substantially non-reactive with other components of the final chewing gum formulation are preferable. Examples of suitable fillers include, without limitation, calcium carbonate, magnesium silicate (i.e., talc), dicalcium phosphate, metallic mineral salts (e.g., alumina, aluminum hydroxide, and aluminum silicates), and combinations thereof. Typically, the gum base comprises from about 0% to about 30% by weight of the filler, and more typically from about 10% to about 20%.

One skilled in the art will appreciate that the gum base need not be prepared from its individual components. For example, the gum base can be purchased with the desired ingredients contained therein, and can be modified to include additional agents. Several manufacturers produce gum bases suitable for use with the described chewing gum compositions. Examples of such gum bases include, without limitation, PHARMGUM™ M, S, or C (SPI Pharma Group; New Castle, Del.). In general, PHARMAGUM™ comprises a mixture of gum base, sweetening agent, plasticizer, and sugar.

In certain instances, the chewing gum composition includes a therapeutic agent centerfill. A centerfill may be particularly suitable when immediate release of the therapeutic agent is preferred. In addition, encapsulating the active therapeutic agent in a centerfill may help to mask any undesirable taste that the therapeutic agent may have. In these instances, the gum base surrounds, at least in part, a centerfill. The centerfill comprises at least one therapeutic agent, and may be a liquid or semi-liquid material. The centerfill material can be a synthetic polymer, a semi-synthetic polymer, low-fat, or fat-free and contain one or more sweetening agents, flavoring agents, coloring agents, and/or scenting agents. Preferably, the centerfill includes a buffer system, including a binary or ternary buffer system as described herein. Methods for preparing a centerfill chewing gum are described, for example, in U.S. Pat. No. 3,806,290, which is hereby incorporated by reference in relevant part.

The chewing gum compositions can have any desired shape, size, and texture. For example, the composition can have the shape of a stick, tab, gumball, and the like. Similarly, the chewing gum can be any desirable color. For example, the chewing gum can be any shade of red, blue, green, orange, yellow, violet, indigo, and mixtures thereof, and can be color coded to indicate the type and dosage of the therapeutic agent therein. The chewing gum can be individually wrapped or grouped together in pieces for packaging by methods well known in the art.

2. Tablets

When the dosage form is a tablet such as a dissolving tablet (i.e., disintegrating tablet) or chewable tablet, the compositions of the present invention comprise a therapeutic agent as described herein derived from one or more gram-positive bacteria, or a pharmaceutically acceptable salt thereof, naturally-occurring immunostimulatory oligodeoxynucleotide, such as a CpG ODN motif or equivalent, an optional promoter, a carrier such as a binder, and a buffer system, including binary or ternary buffer systems. The tablet composition may further comprise lubricating agents, wetting agents, emulsifying agents, suspending agents, preserving agents, sweetening agents, flavoring agents, coloring agents, and disintegrating agents. Typically, the tablet compositions of the present invention comprise from about 0.001% to about 10.0% by weight of the active therapeutic agent (in whatever chosen form, measured as per its free base form), and more typically from about 1.0% to about 5.0%. One skilled in the art understands that the foregoing percentages will vary depending upon the particular source of active therapeutic agent utilized, the amount of the active therapeutic agent desired in the final formulation, as well as on the particular release rate of the active therapeutic agent desired. The buffer system of the tablet composition provides for a final salivary pH in excess of at least about 8.0, preferably at least about 9.5, and more preferably in the range of from about pH 9.9 to about pH 11.

In certain embodiments, the tablet is a dissolving tablet such as a slow-dissolving or quick-dissolving tablet that is dissolved by a subject's saliva, without the need for chewing. For example, a dissolving tablet placed on the subject's tongue can be used for buccal delivery of the therapeutic agent. Alternatively, a dissolving tablet placed underneath the subject's tongue can be used for sublingual delivery of the therapeutic agent. This type of dosage form may be particularly desirable for pediatric and geriatric patients, since small children and aged individuals often have difficulty chewing certain items. Typically, the dissolving tablet is formulated to dissolve within about 1 to about 15 minutes, preferably within about 2 to about 10 minutes, e.g., within about 2, 3, 4, 5, 6, 7, 8, 9, or 10 minutes, following administration. One skilled in the art will understand that quick-dissolving tablets dissolve faster than slow-dissolving tablets, which are typically dissolved gradually rather than rapidly by a subject's saliva. In a preferred embodiment, the slow-dissolving or quick-dissolving tablet delivers the therapeutic agent across the sublingual mucosa over a period of time greater than 1 minute.

In certain other embodiments, the tablet is a chewable tablet that is chewed by a subject and formulated to dissolve either rapidly or gradually. For example, a chewable tablet placed on the subject's tongue can be used for buccal delivery of the therapeutic agent. During chewing, the chewable tablet can be moved around within the mouth and can sometimes be parked between the gums and the cheeks or underneath the tongue. As a result, at least a portion of the therapeutic agent contained within a chewable tablet may also be delivered sublingually (i.e., across the sublingual mucosa). Typically, the chewable tablet is formulated to dissolve within about 1 to about 15 minutes, preferably within about 2 to about 10 minutes and not less than 1 minute, e.g., within about 2, 3, 4, 5, 6, 7, 8, 9, or 10 minutes, following administration.

As described above, the dissolving and chewable tablets of the present invention are typically formulated to dissolve within about 1 to 15 minutes following administration, and preferably not less than about 1 minute. However, while these time frames are amenable to maximum exposure of the therapeutic agent to the oral mucosa (e.g., to the sublingual and/or buccal mucosa), they are not always amenable to user compliance (e.g., users may swallow too frequently and, therefore, hinder maximal transmucosal absorption). Consequently, in certain instances, it may be desirable to strike a balance between patient compliance and maximum exposure time of the therapeutic agent to the oral mucosa. This can be accomplished, for example, by reducing the tablet size (e.g., from about 700-800 mg to about 200-300 mg) without reducing the concentration or amount per unit dose of the buffer system or the therapeutic agent. In addition, subtle changes to the tablet formulation such as, for example, replacing one flavoring agent for another (e.g., chocolate for spearmint) or replacing one binder or sweetening agent for another (e.g., lactose for mannitol or sorbitol) may be used to reduce salivation.

The carrier present in the tablets of the present invention is typically a binder that is useful in keeping the tablet in a semi-solid state, and may be a solid or a liquid, and may for example be a high-melting point fat or waxy material. Materials suitable as binders are discussed in detail above and may be used alone or in combination in the tablet compositions of the present invention. In addition, binders such as mannitol, sorbitol, lactose, sucrose, and inositol can impart properties to the tablet that permit or enhance its disintegration in the mouth.

The tablet composition may further comprise a protecting agent. The protecting agent coats at least part of the therapeutic agent, typically upon the mixing of the two agents. The protecting agent may be mixed with the therapeutic agent in a ratio of from about 0.1 to about 100 by weight, preferably in a ratio of from about 1 to about 50, and more preferably in a ratio of about 1 to about 10. Without being bound to any particular theory, the protecting agent reduces the adhesion between the therapeutic agent and the binder so that the therapeutic agent may be more easily released from the binder. In this way, the therapeutic agent may be delivered across the mucous membranes of the oral cavity within about 5 to about 20 minutes, preferably within about 10 minutes. Materials suitable as protecting agents are discussed in detail above and may be used alone or in combination in the tablet compositions of the present invention.

The tablet composition may also comprise one or more elastomeric solvents such as rosins and resins. Non-limiting examples of such solvents are discussed in detail above and may be used alone or in combination in the tablet compositions of the present invention. In addition, the tablet composition may further comprise waxes such as beeswax and microcrystalline wax, fats or oils such as soybean and cottonseed oil, and combinations thereof. Moreover, the tablet composition may additionally include plasticizers such as softeners or emulsifiers. Such plasticizers may, for example, help reduce the viscosity of the salivary solution of the dissolved tablet to a desirable consistency and improve its overall texture and bite and help facilitate the release of the therapeutic agent. Non-limiting examples of such plasticizers are discussed in detail above and may be used alone or in combination in the tablet compositions of the present invention.

In certain instances, the tablet composition includes a therapeutic agent centerfill. A centerfill may be particularly suitable when immediate release of the therapeutic agent is preferred. In addition, encapsulating the active therapeutic agent in a centerfill may help to mask any undesirable taste that the therapeutic agent may have. In these instances, the binder surrounds, at least in part, a centerfill. The centerfill comprises at least one therapeutic agent in accordance with the present disclosure, and may be a liquid or semi-liquid material. The centerfill material can be low-fat or fat free and contain one or more sweetening agents, flavoring agents, coloring agents, and/or scenting agents. Preferably, the centerfill includes a binary or ternary buffer system as described herein.

In certain other instances, the tablet composition of the present invention is multilayered. In this way, the dissolving or chewable tablet can be designed to provide more than one therapeutic agent, e.g., two or more active therapeutic agents, or one or more active therapeutic agents derived from a first gram-positive bacteria in combination with one or more active therapeutic agents derived from a second gram-positive bacteria. For example, with a bi-layered tablet, the first layer contains a first active therapeutic agent derived from a first gram-positive bacteria, and the second layer contains the same or a different active therapeutic agent derived from the same or a different gram-positive bacteria. Typically, the first layer comprises the dissolving or chewable portion of the tablet, and the second (i.e., subsequent) layer is coated by the first layer. This type of formulation may be particularly suitable when immediate release of the active therapeutic agent, followed by gastrointestinal absorption of a second therapeutic agent, is desirable. Gastrointestinal absorption of the second therapeutic agent may be desirable, for example, in order to mitigate co-morbid symptoms or to sustain the therapeutic benefit of the active therapeutic agent in the dissolving or the chewable portion of the tablet. Alternatively, the second layer is present as a layer lateral to the first layer. The second layer typically comprises at least one therapeutic agent, and can also comprise one or more sweetening agents, flavoring agents, coloring agents, and scenting agents as described above. In some instances, the second layer further includes a binary or ternary buffer system as described herein.

In still other instances, the combination of the active therapeutic agent with or without additional therapeutic agents need not take the form of a multilayered tablet, but instead comprises a single homogenous tablet layer. This type of formulation may also be used in the case where gastrointestinal absorption of at least one therapeutic agent is desirable. In this case, the relative extent of ionization of the two or more therapeutic agents determines how they are to be absorbed. For example, those therapeutic agents that are un-ionized are absorbed through the oral mucosa, while the ionized agents are swallowed for gastrointestinal absorption.

The tablet compositions can have any desired shape, size, and texture. For example, the tablet can have the shape of a stick, tab, pellet, sphere, and the like. Similarly, the tablet can be any desirable color. For example, the tablet can be any shade of red, blue, green, orange, yellow, violet, indigo, and mixtures thereof, and can be color coded to indicate the type and dosage of the therapeutic agent therein. The tablets can be individually wrapped or grouped together in pieces for packaging by methods well known in the art.

3. Lozenges

When the dosage form is a lozenge or candy, the compositions of the present invention comprise the active agent from a gram positive bacteria or a pharmaceutically acceptable salt thereof, an optional promoter, a carrier such as a binder, and a buffer system, including a binary or ternary buffer system; the lozenge or candy composition may further comprise lubricating agents, wetting agents, emulsifying agents, suspending agents, preserving agents, sweetening agents, flavoring agents, coloring agents, and disintegrating agents. A general discussion of lozenges and candies is provided, for example, in "Pharmaceutical Dosage Forms, Volume 1: Tablets" [2nd Ed., Marcel Dekker, Inc., New York, N.Y., pages 75-418 (1989)].

Typically, the lozenge or candy compositions of the present invention comprise from about 0.001% to about 10.0% by weight of the active therapeutic agent (in whatever chosen form, measured as per its free base form), preferably from about 1.0% to about 5.0%, and more preferably from about 2.5% to about 4.5%. One skilled in the art understands that the foregoing percentages will vary depending upon the particular source of the active therapeutic agent utilized, the amount of the active therapeutic agent desired in the final formulation, as well as on the particular release rate of the active therapeutic agent desired. The buffer system for the lozenge or candy composition, when included or necessary, may be a single-compound buffer system, but is typically a binary or ternary buffer system comprising amorphous magnesium oxide or the like with a carbonate salt and/or a bicarbonate salt. For example, an exemplary ternary buffer system typically comprises from about 4.0% to about 7.0% by weight sodium carbonate; from about 8.0% to about 12.0% by weight dessicant-coated sodium bicarbonate; and from about 20% to about 30% by weight amorphous magnesium oxide. The buffer system provides for a final salivary pH in excess of at least about 8.0 when necessary, preferably at least about 9.5, and more preferably in the range of from about 9.9 to about 11.

In certain embodiments, the lozenge or candy is dissolved by a subject's saliva, without the need for chewing. For example, a lozenge placed on the subject's tongue can be used for buccal delivery of the therapeutic agent. Alternatively, a lozenge placed underneath the subject's tongue can be used for sublingual delivery of the therapeutic agent. This type of dosage form may be particularly desirable for pediatric and geriatric patients, since small children and aged individuals often have difficulty chewing certain items. Typically, the lozenge is formulated to dissolve within about 1 to about 15 minutes, preferably within about 2 to about 10 minutes, and preferably not less than about 1 minute, e.g., within about 2, 3, 4, 5, 6, 7, 8, 9, or 10 minutes, following administration. In a preferred embodiment, the lozenge or candy delivers the therapeutic agent across the sublingual mucosa in a period of time greater than 1 minute.

As described above, the lozenges the present invention are typically formulated to dissolve within about 1 to about 15 minutes following administration, and preferably not less than about 1 minute. However, while these time frames are amenable to maximum exposure of the therapeutic agent to the oral mucosa (e.g., to the sublingual and/or buccal mucosa), they are not always amenable to user compliance (e.g., users may swallow too, frequently and, therefore, hinder maximal transmucosal absorption). Consequently, in certain instances, it may be desirable to strike a balance between patient compliance and maximum exposure time of the therapeutic agent to the oral mucosa. This can be accomplished, for example, by reducing the lozenge size (e.g., from about 700-800 mg to about 200-300 mg) without reducing the concentration or the amount per unit dose of the buffer system or the therapeutic agent. In addition, subtle changes to the lozenge formulation such as, for example, replacing one flavoring agent for another (e.g., chocolate for spearmint) or replacing one binder or sweetening agent for another (e.g., lactose for mannitol or sorbitol) may be used to reduce salivation.

The carrier present in the lozenges of the present invention is typically a binder that is useful in keeping the lozenge in a semi-solid state, and may be a solid or a liquid, and may for example be a high-melting point fat or waxy material. Materials suitable as binders are discussed in detail above and may be used alone or in combination in the lozenge compositions of the present invention. In addition, binders such as mannitol, sorbitol, lactose, sucrose, and inositol can impart properties to the lozenge that permit or enhance its disintegration in the mouth.

The lozenge composition may further comprise a protecting agent. The protecting agent coats at least part of the therapeutic agent, typically upon the mixing of the two agents. The protecting agent may be mixed with the therapeutic agent in a ratio of from about 0.1 to about 100 by weight, preferably in a ratio of from about 1 to about 50, and more preferably in a ratio of about 1 to about 10. Without being bound to any particular theory, the protecting agent reduces the adhesion between the therapeutic agent and the binder so that the therapeutic agent may be more easily released from the binder. In this way, the therapeutic agent may be delivered across the mucous membranes of the oral cavity within about 5 to about 20 minutes, preferably within about 10 minutes. Materials suitable as protecting agents are discussed in detail above and may be used alone or in combination in the lozenge compositions of the present invention.

The lozenge composition may also comprise one or more elastomeric solvents such as rosins and resins. Non-limiting examples of such solvents are discussed in detail above and may be used alone or in combination in the tablet compositions of the present invention. In addition, the lozenge composition may further comprise waxes such as beeswax and microcrystalline wax, fats or oils such as soybean and cottonseed oil, and combinations thereof. Moreover, the lozenge composition may additionally include plasticizers such as softeners or emulsifiers. Such plasticizers may, for example, help reduce the viscosity of the salivary solution of the dissolved lozenge to a desirable consistency and improve its overall texture and bite and help facilitate the release of the therapeutic agent. Non-limiting examples of such plasticizers are discussed in detail above and may be used alone or in combination in the lozenge compositions of the present invention.

In certain instances, the lozenge composition includes a therapeutic agent centerfill. A centerfill may be particularly suitable when immediate release of the therapeutic agent is preferred. In addition, encapsulating the therapeutic agent in a centerfill may help to mask any undesirable taste that the therapeutic agent may have. In these instances, the binder surrounds, at least in part, a centerfill. The centerfill comprises at least one therapeutic agent, and may be a liquid or semi-liquid material. The centerfill material can be a synthetic polymer, a semi-synthetic polymer, low-fat, or fat free and contain one or more sweetening agents, flavoring agents, coloring agents, and/or scenting agents. Preferably, the centerfill includes a binary or ternary buffer system as described herein.

In certain other instances, the lozenge composition of the present invention is multilayered. In this way, the lozenge can be designed to provide more than one therapeutic agent, e.g., two or more the therapeutic agents, or one or more the therapeutic agent derived from a first gram-positive bacteria, in combination with one or more therapeutic agents derived from a second gram-positive bacteria. For example, with a bi-layered lozenge, the first layer contains may contain a first therapeutic agent derived from *Lactobacillus*, and the second layer contains the same or different therapeutic agent or therapeutic agent derived from the same or a second gram-positive bacteria, such as a naturally-occurring CpG ODN or a motif thereof. Typically, the first layer comprises the dissolving portion of the lozenge, and the second (i.e., subsequent) layer is coated by the first layer. This type of formulation may be particularly suitable when immediate release of the therapeutic agent, followed by gastrointestinal absorption of a second therapeutic agent, is desirable. Gastrointestinal absorption of the second therapeutic agent may be desirable, for example, in order to mitigate co-morbid symptoms or to sustain the therapeutic benefit of the primary therapeutic agent in the dissolving portion of the lozenge. Alternatively, the second layer is present as a layer lateral to the first layer. The second layer typically comprises at least one therapeutic agent, and can also comprise one or more sweetening agents, flavoring agents, coloring agents, and scenting agents as described above. In some instances, the second layer further includes a buffer system as described herein.

In still other instances, the combination of the therapeutic agents with or without non-bacterial therapeutic agents need not take the form of a multilayered lozenge, but instead comprises a single homogenous lozenge layer. This type of formulation may also be used in the case where gastrointestinal absorption of at least one therapeutic agent is desirable. In this case, the relative extent of ionization of the two or more therapeutic agents determines how they are to be absorbed. For example, those therapeutic agents that are un-ionized are absorbed through the oral mucosa, while the ionized agents are swallowed for gastrointestinal absorption.

The lozenge compositions can have any desired shape, size, and texture. For example, the lozenge can have the shape of a stick, tab, pellet, sphere, and the like. Similarly, the lozenge can be any desirable color. For example, the lozenge can be any shade of red, blue, green, orange, yellow, violet, indigo, and mixtures thereof, and can be color coded to indicate the type and dosage of the therapeutic agent therein. The lozenges can be individually wrapped or grouped together in pieces for packaging by methods well known in the art.

In addition to the preferred dosage forms described above, the compositions of the present invention can also take to form of a solution formulation for delivery of a therapeutic agent as described herein across the oral mucosa. For example, the solution formulation can be administered sublingually by using a two-chamber syringe delivery system, in which the upper chamber contains an unbuffered therapeutic agent solution, the lower chamber contains the dry buffer system components, and a non-permeable membrane separates the upper and lower chambers. Depressing the syringe ruptures the non-permeable membrane and allows mixing of the unbuffered therapeutic agent solution with the dry buffer system components. The resulting buffered therapeutic agent solution is then released from the tip of the syringe. As such, by simply placing the tip of the syringe anywhere underneath a subject's tongue and depressing the syringe, a solution formulation of the present invention can be used to deliver the active therapeutic composition across the subject's sublingual mucosa.

Accordingly, the present invention further provides a composition for delivery of a therapeutic composition across the oral mucosa of a subject for the treatment of a hepatic disease and/or disorder, the composition comprising: (a) a gram-positive bacteria extract, lysate, or a pharmaceutically acceptable salt thereof, preferably from the *Lactobacillus* species of gram-positive bacteria; (b) a naturally-occurring immunostimulatory oligodeoxynucleotide; (c) an optional, active agent promoter; and, optionally, (d) a buffer system comprising a carbonate salt and/or a bicarbonate salt, wherein the buffer system raises the pH of saliva to a pH greater than about 9.9 irrespective of the starting pH of saliva. Preferably, the composition is a solution that is prepared just prior to administration to the oral mucosa. In certain preferred embodiments, the buffer system comprises sodium bicarbonate and sodium carbonate wherein the ratio of sodium bicarbonate to sodium carbonate ranges from about 1:1 to about 5:1 by weight. In other embodiments, sodium carbonate is used in an amount that is equivalent to, or in excess of sodium bicarbonate. More particularly, the compositions are those that provide peak plasma levels of the active ingredient in less than 15 minutes (e.g, about 1 to about 15 minutes), preferably in about 5 minutes to about 10 minutes.

D. Methods of Administration

The compositions of the present invention are useful in therapeutic applications, e.g., for treating immune diseases or disorders, including hepatic diseases or disorders, such as hepatitis A, B and/or C, in subjects in need of such treatment. The methods of the present invention are useful in the treatment of a variety of hepatic disorders, in particular those characterized by an associated link with the alternative pathway in the complement system of the subject. Therefore, according to the present disclosure, a hepatic disorder is any liver disease or disorder in the liver or the surrounding vasculature. For example, the methods and compositions of the present invention are useful in the treatment of a variety of hepatic disorders, including those resulting from infection, iatrogenic disorders, hereditary disorders, autoimmune disorders, cholestatic syndromes, sarcoidosis, organ transplantation, hepatic cancer, and the like.

Diseases or disorders within the scope of the present disclosure include, but are not limited to, the diseases and disorders detailed in Table 1.

TABLE 1

Systemic Diseases and Disorders Involving Liver Inflammation

A. Hepatitis
1. Any inflammation of the liver, as for example in acute hepatitis, chronic hepatitis, alcoholic hepatitis and cirrhosis.
2. Infection
Any inflammation of the liver resulting from infection, especially viral infection, especially chronic viral hepatitis, for example inflammation associated with:
a) Hepatitis A, picorna virus,
b) Hepatitis B, hepadna virus (hepatocellular carcinoma),
c) Hepatitis C, flavivirus,
d) Hepatitis D (Δ), incomplete RNA virus (requires co-infection with hepatitis B),
e) Hepatitis E, single stranded, positive sense RNA genome,
f) Hepatitis F,
g) Hepatitis G (HGBV-C) single stranded RNA virus,
h) Epstein-Barr virus,
i) cytelomegalovirus,
j) adenovirus,
k) other viral infections of the liver
3. Autoimmune
Any inflammation of the liver associated with autoimmune onset of known or unknown etiology, typically associated with significant lymphocyte infiltration in the portal tracts and associated piecemeal necrosis.
4. Iatrogenic
Any drug induced liver inflammation, including for example chronic active hepatitis, cholestasis or granuloma formation.
5. Hereditary
Any inflammation associated with gene-linked trait, for example cirrhotic changes in the liver associated with hepatolenticular degeneration,
a) Wilson's disease
b) α1-antitrypsin deficiency
c) other inherited metabolic disorders, for example, galactosemia.
B. Cholestatic Syndromes
Any inflammation of the intrahepatic bile ducts, including those resulting in hepatic dysfunction and cirrhosis as for example in primary biliary cirrhosis, primary sclerosing cholangitis and adult idiopathic ductopenia.
C. Transplantations
Any inflammation of the liver or hepatic ducts including that associated with hepatic transplantation, liver injury in graft versus host disease and recipients of renal and other allografts, for example hyperacute allograft rejection, and xenograft rejection.

Other disorders or diseases that may be prevented, ameliorated, and/or treated with the compositions of the present invention include cancer and tumors within a subject. The term "cancer" as used herein refers to a malignant neoplasm that has undergone characteristic anaplasia with loss of differentiation, increase rate of growth, invasion of surrounding tissue, and is capable of metastasis. For example, thyroid cancer is a malignant neoplasm that arises in or from thyroid tissue, and breast cancer is a malignant neoplasm that arises in or from breast tissue (such as a ductal carcinoma). Residual cancer is cancer that remains in a subject after any form of treatment given to the subject to reduce or eradicate thyroid cancer. Metastatic cancer is a cancer at one or more sites in the body other than the site of origin of the original (primary) cancer from which the metastatic cancer is derived. Cancer includes, but is not limited to, solid tumors.

The term "tumor" as used herein refers to an abnormal growth of cells, which can be benign or malignant. Cancer is a malignant tumor, which is characterized by abnormal or uncontrolled cell growth. Other features often associated with malignancy include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system.

The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include but are not limited to fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma and retinoblastoma). In several examples, a tumor is melanoma, lung cancer, lymphoma breast cancer or colon cancer.

The compositions described herein, when used in the treatment of one or more cancer types, or tumors, may optionally include, or be combined with, one or more other anti-cancer agents, or compounds. Such anti-cancer agents include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide;

anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTEA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; brapirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARO 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A-4 (including combretastatin A-4 diphosphate); combretastatin analogues; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epothilone A; epothilone B; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galoc tabine; ganirelix; gelatinase inhibitors; gemcitabine; glutathione inhibitors; HMG CoA reductase inhibitors (e.g., atorvastatin, cerivastatin, fluvastatin, lescol, lupitor, lovastatin, rosuvastatin, and simvastatin); hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; LFA-3TIP (Biogen, Cambridge, Mass.; U.S. Pat. No. 6,162,432); liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MWF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl-lipid A+myobacterium cell wall sk; mopidamol; multiple drug resistance gene inhibitor; multiple tumor suppressor 1-based therapy; mustard-type anticancer agents; mycaperoxide B; mycobacterial cell wall extract; myriaporone; N-acetyldinaline; N-substituted benzamides; nafarelin; nagrestip; naloxone+ pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil (5-FU); leucovorin; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; thalidomide; velaresol; veramine; verdins; verteporfin; vinorelbine; vinxaltine; vorozole; zanoterone; zeniplatin; zilascorb; and zinostatin stimalamer.

Still another disorder that may be treatable with the compositions of the present invention includes Lyme disease and other tick-borne infections, including anemia caused by

*Babesia microti, Ehrlichiosis, tularemia* (such as that caused by *Francisella tularensis*) and diseases caused by *Rikettsia rickettsii.*

Particularly preferred disorders within the context of the invention are chronic hepatitis particularly hepatitis resulting from infection, particularly viral infection. Included in this category are the established serological categories of chronic hepatitis, including viral (HBV, HDV, HCV), autoimmune hepatitis (classic lupoid type and subtypes), autoimmune overlap syndromes, drug induced (for example nitrofurantoin, alpha methyldopa, isoniazid) and so-called "cryptogenic" hepatitis In this regard, the skilled artisan will make reference to chapters 8 and 9, and especially Tables 9.2 and 9.3 in "McSween's Pathology of the Liver, 5th Edition (Id.). As the skilled artisan will recognize, some chronic liver diseases not included within the definition of chronic hepatitis may have histological features of chronic hepatitis (for example, piecemeal necrosis). These disorders such as, for example, diseases of intra or extrahepatic bile ducts, are included within the definition herein. Infection with a number of viruses is known to result in serious inflammation of the liver including the hepatitis viruses, hepatitis A (HAV), hepatitis B (HBV), hepatitis C (HCV), hepatitis D (HDV, delta agent) hepatitis E, hepatitis F and other viruses such as Epstein-Barr virus, cytomegalovirus, adenovirus, paramyovirus, and the like. At least seven types of hepatitis virus (designated A-G) have been identified to date. Of these, one of the most devastating is hepatitis C virus (HCV, also called non-A, non-B). An estimated 3.9 million people in the US are currently infected with HCV, and an estimated 8,000-10,000 deaths each year result from HCV-associated chronic liver disease. Current therapies include γ-interferon, emphasize B and ribivirin, each of which have limited efficacy and serious side effects on the patients. Current therapy also includes transplantation, however, since the infected individual remains infected with the virus, post-transplant immunosuppressed patients exhibit increased viral RNA levels and often rapidly progress to liver disease with the new liver.

Chronic cholestatic syndromes are characterized by progressive inflammatory destruction of intrahepatic bile ducts resulting in hepatic dysfunction, fibrosis and cirrhosis. Examples of this type of disorder include primary biliary cirrhosis, primary sclerosing cholangitis and adult idiopathic ductopenia.

Hereditary disorders treatable by the methods disclosed herein include those inflammatory disorders associated with a gene-linked trait. Examples include but are not limited to Wilson's disease, α1-antitrypsin deficiency and inherited metabolic disorders such as galactosemia and tyrosineanemia.

Importantly, the compositions of the present invention provide the rapid delivery of an active therapeutic agent composition of the present disclosure across the oral mucosa, irrespective of the starting pH of saliva. In particular, the delivery of the therapeutic agent across the oral mucosa avoids hepatic first pass metabolism, degradation within the gastrointestinal tract, and therapeutic agent loss during absorption. As a result, the therapeutic agent reaches the systemic circulation in a substantially shorter period of time and at a substantially higher concentration than with traditional oral (e.g., tablet) administration.

The compositions of the present invention have particular utility in the area of human and veterinary therapeutics. Generally, administered dosages will be effective to deliver picomolar to micromolar concentrations of the active composition to the appropriate site.

Administration of the compositions of the present invention may preferably carried out via any of the accepted modes of administration to the mucous membranes of the oral cavity. Examples of suitable sites of administration within the oral mucosa include, without limitation, the mucous membranes of the floor of the mouth (sublingual mucosa), the cheeks (buccal mucosa), the gums (gingival mucosa), the roof of the mouth (palatal mucosa), the lining of the lips, and combinations thereof. These regions differ from each other with respect to their anatomy, drug permeability, and physiological response to drugs. Preferably, the compositions of the present invention are administered to the sublingual mucosa, buccal mucosa, or a combination thereof.

The oral mucosa, possessing a rich blood supply and suitable drug permeability, is an especially attractive route of administration for systemic delivery of therapeutic agents. Furthermore, delivery of a therapeutic agent across the oral mucosa bypasses hepatic first pass metabolism, avoids enzymatic degradation within the gastrointestinal tract, and provides a more suitable enzymatic flora for drug absorption. As used herein, the term "sublingual delivery" refers to the administration of a therapeutic agent across the mucous membranes lining the floor of the mouth and/or the ventral tongue. The term "buccal delivery" as used herein refers to the administration of a therapeutic agent across the mucous membranes lining the cheeks.

The oral mucosa is composed of an outermost layer of stratified squamous epithelium. Beneath this layer lies a basement membrane, i.e., the lamina propria, followed by the submucosa as the innermost layer. The epithelium of the oral mucosa is similar to the stratified squamous epithelia found in the rest of the body in that it contains a mitotically active basal cell layer, advancing through a number of differentiating intermediate layers to the superficial layers, where cells are shed from the surface of the epithelium. For example, the epithelium of the buccal mucosa is about 40-50 cell layers thick, while that of the sublingual epithelium contains somewhat fewer cell layers. The epithelial cells increase in size and become flatter as they travel from the basal layers to the superficial layers.

The turnover time for buccal mucosal epithelium, estimated at 5-6 days, is representative of the turnover time for sublingual mucosal epithelium as well as other epithelia in the oral mucosa [Harris, et al., J. Pharm. Sci, Vol. 81, pp. 1-10 (1992)]. The thickness of the oral mucosa varies depending on the site in the oral cavity. For example, the buccal mucosa measures at about 500-800 μm in thickness, while the hard and soft palatal mucosa, the sublingual mucosa, the ventral tongue, and the gingival mucosa measure at about 100-200 μm in thickness. The composition of the epithelium also varies depending on the site in the oral cavity. For example, the mucosae of areas subject to mechanical stress (i.e., the gingivae and hard palate) are keratinized similar to the epidermis. However, the mucosae of the soft palate, the sublingual region, and the buccal region are not keratinized [Harris et al., supra]. The keratinized epithelia contain neutral lipids like ceramides and acylceramides, which have been associated with providing a barrier function. As a result, these epithelia are relatively impermeable to water. In contrast, non-keratinized epithelia, such as sublingual and buccal epithelia, do not contain acylceramides and have only small amounts of ceramide [Wertz, et al., Crit. Rev. Ther. Drug Carr. Sys., Vol. 8, pp. 237-269 (1991); Squier, et al., J. Invest. Dermat., Vol. 96, pp. 123-126 (1991); Squier, et al., in "Oral Mucosal Drug Delivery," Ed. M. J. Rathbone, Marcel Dekker, Inc., New York, N.Y., pp. 1-26 (1996)]. Non-keratinized epithelia also contain small amounts of neutral but polar lipids, e.g., cholesterol sulfate and glucosyl ceramides. As such, these epithelia have been found to be considerably more permeable to water than keratinized epithelia.

In general, the oral mucosa is a somewhat leaky epithelia intermediate between that of the epidermis and intestinal mucosa. For example, the permeability of the buccal mucosa is estimated to be about 4-4000 times greater than that of skin [Galey, et al., J. Invest. Dermat., 67:713-717 (1976)]. The permeability of different regions of the oral mucosa generally decrease in the order of sublingual mucosa greater than buccal mucosa, and buccal mucosa greater than palatal mucosa. This permeability is generally based upon the relative thickness and degree of keratinization of these membranes, with the sublingual mucosa being relatively thin and non-keratinized, the buccal mucosa being thicker and non-keratinized, and the palatal mucosa being intermediate in thickness, but keratinized.

The epithelial cells of the oral mucosa are surrounded by mucus comprising primarily complexes of proteins and carbohydrates that may or may not be attached to certain regions on the cell surface. The mucus may play a role in cell-cell adhesion, as well as acting as a lubricant, allowing cells to move relative to one another [Tabak et al., J. Oral Pathol., 11:1-17 (1982)]. In stratified squamous epithelia found elsewhere in the body, mucus is synthesized by specialized mucus secreting cells such as goblet cells; however, in the oral mucosa, mucus is secreted by the major and minor salivary glands as part of saliva [Tabak, et al., supra; Rathbone, et al., Adv. Drug Del. Rev., 13:1-22 (1994)]. At physiological pH, the mucus network carries a negative charge due to the sialic acid and sulfate residues present on the carbohydrates. At this pH, mucus can form a strongly cohesive gel structure that binds to the epithelial cell surface as a gelatinous layer. Without being bound to any particular theory, the buffer systems of the present invention neutralize the sialic acid residues present on the carbohydrates and prevent them from interacting with the therapeutic agent, thereby further enhancing drug permeation.

Another feature of the environment of the oral cavity is the presence of saliva produced by the salivary glands. Saliva is the protective fluid for all tissues of the oral cavity. Saliva is an aqueous fluid with about 1% organic and inorganic materials. The major determinant of the salivary composition is the flow rate, which in turn depends upon factors such as the time of day, the type of stimulus, and the degree of stimulation. The salivary pH typically ranges from about 5.5 to about 7.0, depending on the flow rate. For example, at high flow rates, the sodium and bicarbonate concentrations increase, leading to an increase in the pH. Because the daily salivary volume is between about 0.5 to about 2 liters, the oral cavity provides an aqueous environment for the hydration and/or dissolution of the oral mucosal dosage forms of the present invention.

The sublingual mucosa is the most highly permeable region of the oral cavity, and provides rapid absorption and high bioavailability of a drug in a convenient, accessible, and well-accepted route of administration [Harris, et al., supra]. Suitable sublingual dosage forms include, without limitation, tablets (e.g., quick-dissolving, slow-dissolving), lozenges, candy, and soft gelatin capsules filled with liquid drug. Such systems create a very high drug concentration in the sublingual region before they are systemically absorbed across the sublingual mucosa. As a result, the sublingual mucosa is particularly well-suited for producing a rapid onset of action, and sublingual dosage forms can be used to deliver drugs with shorter delivery period requirements and/or less frequent dosing regimens. Although the buccal mucosa is considerably less permeable than the sublingual area, rapid absorption and high bioavailability of a drug can also be observed with buccal administration. Suitable buccal dosage forms include, without limitation, chewing gums, tablets (e.g., quick-dissolving, slow-dissolving), lozenges, candy, and the like. Both the buccal mucosa and the sublingual mucosa are far superior to the gastrointestinal tract for providing increased absorption and bioavailability of a drug.

To increase the permeability of drugs through the oral mucosa, penetration enhancers can be included in the dosage forms of the present invention. The penetration enhancers may be of the type that alters the nature of the oral mucosa to enhance penetration, or of the type that alters the nature of the therapeutic agent to enhance penetration through the oral mucosa. Suitable penetration enhancers include, without limitation, polyoxyethylene 23-lauryl ether, aprotin, azone, benzalkonium chloride, cetylpyridinium chloride, cetyltrimethylammonium bromide, cyclodextrin, dextran sulfate, lauric acid, propylene glycol, lysophosphatidylcholine, menthol, methoxysalicylate, methyloleate, oleic acid; phosphatidylcholine, polyoxyethylene, polysorbate 80, sodium ethylenediaminetetraacetic acid ("EDTA"), sodium deoxycholate, sodium glycocholate, sodium glycodeoxycholate, sodium lauryl suflate, sodium salicylate, sodium taurocholate, sodium taurodeoxycholate, as well as certain sulfoxides and glycosides, and combinations thereof.

It should be noted that while delivery through the oral mucosa is preferred in accordance with the present disclosure, any method of delivery that delivers the active therapeutic agent to the mucosal wall where it can begin to act therapeutically is envisioned, such alternative mucosal delivery formulations including but not limited to suppositories (both rectal and vaginal), sprays (both oral and nasal), subdermal implants, and controlled release capsules that allow the formulation to move past the stomach region of the patient, e.g., pH controlled release capsules.

While not wishing to be limited or restricted by theory, it is believed that the naturally-occurring CpG oligodeoxynucleotides (CpG ODNs) have the potential to enhance the antigen-presenting cells function of human native B cells, particularly those for different Hepatic viruses, such as Hepatitis B virus (HBV) epitopes, as shown through binding capacity studies. These results could suggest new strategies for development of vaccine design, and provide a less toxic therapeutic regimen for patients in need thereof.

The following examples are included to demonstrate preferred embodiments of the inventions. It should be appreciated by those of skill in the art that the techniques disclosed in the examples which follow represent techniques discovered by the inventors to function well in the practice of the inventions, and thus can be considered to constitute preferred modes for its practice. However, those of skill in the art should, in light of the present disclosure, appreciate that many changes can be made in the specific embodiments which are disclosed and still obtain a like or similar result without departing from the scope of the inventions.

EXAMPLES

Example 1: Active Ingredient Composition Preparation

In order to prepare an exemplary formulation as described herein suitable for therapeutic testing and further cell line testing, such as in screening tests and subject testing.

Active Ingredient. The active ingredient is a gram positive bacteria, such as described herein above. In example, *Lactobacillus delbrueckii*, ssp. *Bulgaricus* was used, employing a fermentation and cell isolation process as carried out by Kerry Ingredients & Flavours (Beloit, Wis.) and as described generally below.

Fermentation. Cells of a gram positive bacteria, *Lactobacillus delbrueckii* subsp. *Bulgaricus*, was fermented in 500 L of an appropriate media for approximately 120 hours.

Cell Isolation. The 500 L of broth was centrifuged and the resultant cell mass was washed three times with DI water. This produced approximately 60 kg of wet cell mass.

Lysing and Purification. The wet cell mass was reconstituted and the pH is adjusted to 6.8-7.0. Lysozyme chloride (extracted from hen egg whites) was added to make a solution with a concentration of 500 ppm of lysozyme chloride. The slurry was agitated and the temperature is maintained at 40-50° C. for 24 hours. After lysing, the active components were in the liquid phase. This liquid material containing the water soluble active components was recovered through centrifugation to remove the solid material, and then washed three times with DI water. The resultant mixture was frozen in pellets and the remaining solid material in the centrifuge was discarded.

Formulation. The frozen pellets were freeze dried to form a dry powder and milled, as necessary. This material was blended with a promoter, such as N-acetyl D-glucosamine HCl (NAG), to form a mixture of lysed *Lactobacillus delbrueckii* subsp. *Bulgaricus* and NAG. Optionally, other formulation excipients to generate a solid form pill or powder were added, as appropriate. This product was then used in the following screening tests.

Example 2: TLR Screening

TLR stimulation was tested by assessing NF-κB activation in HEK293 cells expressing a given TLR or NLR. The activities of the samples were tested on seven different human TLRs: TLR2, 3, 4, 5, 7, 8 and 9 (Invivogen, San Diego, Calif.), and on two different human NLRs (NOD1 and NOD2). Each ligand was tested at a final concentration of 1/100 of the stock solution on the TLR or NLR cells, and compared to control ligands, as described below. This step was performed in triplicate.

The control ligands, control cell lines, and sample product used in the examples were as shown in Table 2.

TABLE 2

Control ligands and control cell line information used in ligand screening tests.

| | |
|---|---|
| Control Ligands | TLR2: HKLM (heat-killed *Listeria monocytogenes*) at $10^8$ cells/mL. |
| | TLR3: Poly(I:C) at 1 μg/mL |
| | TLR4: E. coli K12 LPS at 100 ng/mL |
| | TLR5: |
| | TLR7: CL097 at 1 μg/mL |
| | TLR8: CL075 at 1 μg/mL |
| | TLR9: CpG ODN 2006 at 100 ng/mL |
| | NOD1: C12iEDAP at 10 μg/mL |
| | NOD2: L18-MDP at 100 ng/mL |
| Control Cell Lines | HEK293/Null1: TNFα at 1 μg/mL (control for human TLR 2, 3, 5, 8, 9 and NOD 1) |
| | HEK293/Null1-k: TNFα at 1 μg/mL (control for human TLR7) |
| | HEK293/Null2: TNFα at 1 μg/mL (control for human TLR4 and NOD2) |
| Sample | Lysate of *Lactobacillus delbrueckii* subsp. *Bulgaricus* (1/10 dilution prepared in sterile, endotoxin-free water) |

General Procedure.

TLR stimulation in the screening is tested by assessing NF-κB activation in the HEK293 cells expressing a given TLR. The secreted alkaline phosphatase reporter is under the control of a promoter inducible by the transcription factor NF-κB. TLR stimulation in the screening was tested by assessing NF-κB activation in the HEK293 cells expressing a given TLR or NLR. This reporter gene allows the monitoring of signaling through the TLR/NLR, based on the activation of NF-κB. In a 96-well plate (200 μL total volume) containing the appropriate cells (50,000-75,000 cells/well), 20 μL of the Sample (lysate product) or the positive control ligands to the wells. The media added to the wells is designed for the detection of NF-κB induced SEAP (secreted alkaline phosphatase) expression. After a 16-20 hr incubation, the OD (optical density) at 650 nm was read on an Molecular Devices Spectra Max 340PC absorbance detector and recorded.

Figure 3:
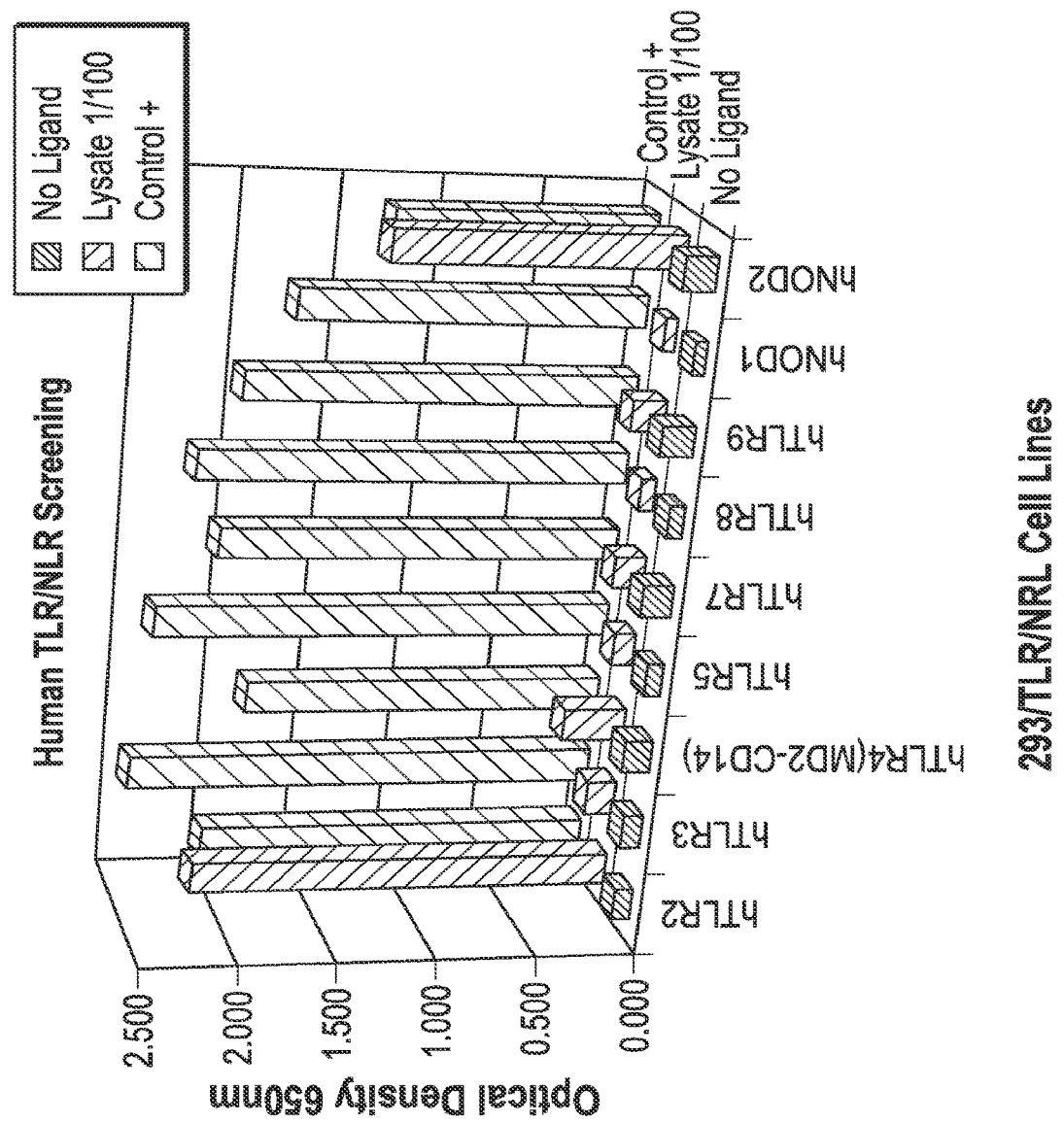
FIG. 3 illustrates a graph of exemplary stimulatory effects of a composition of the present invention on select TLR/NLR cell lines; the values in the graph correspond to an average of screenings 1-3.
Figure 4:
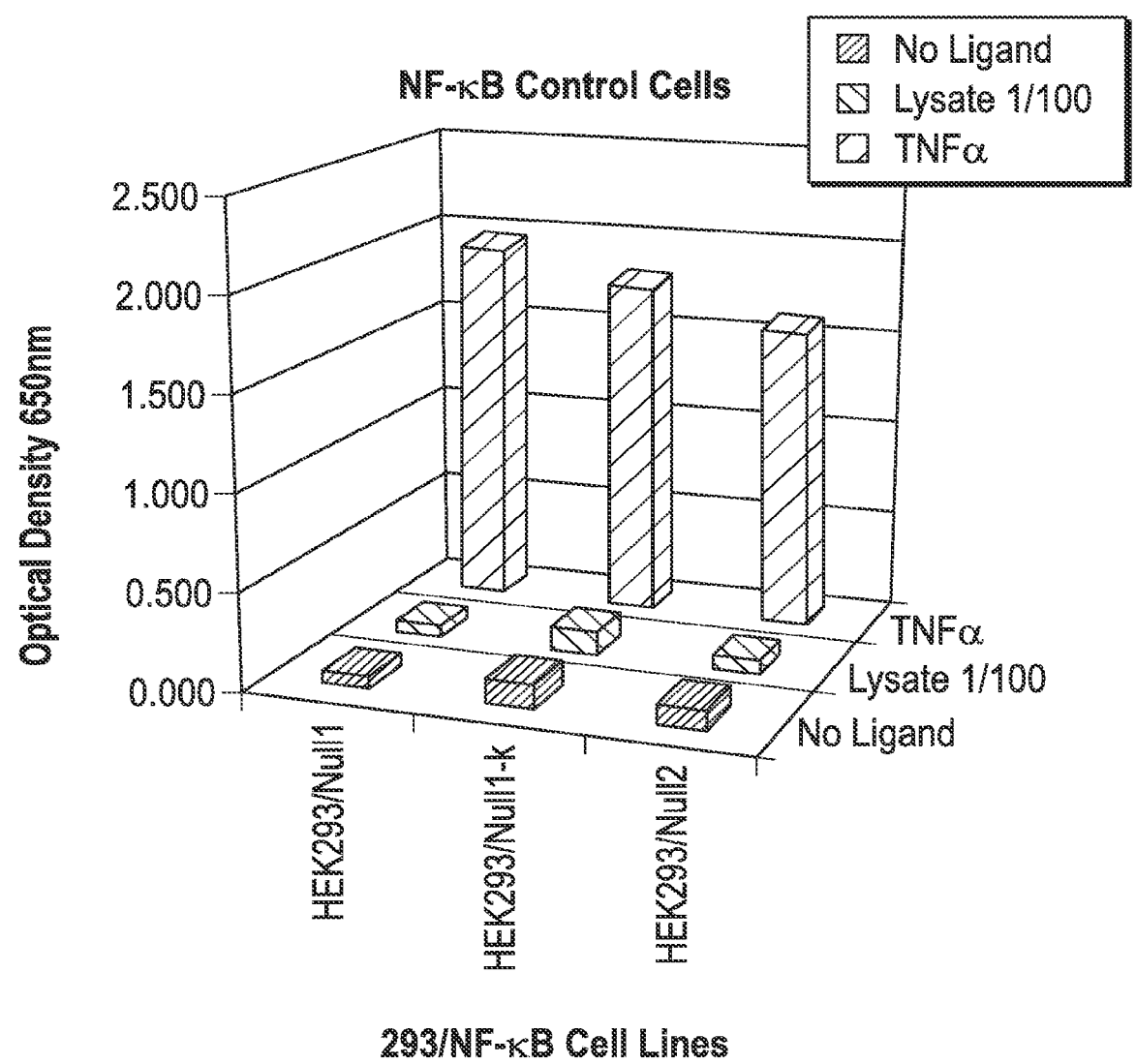
FIG. 4 illustrates a graph of stimulatory effects of control and sample compositions of the present invention against NF-κB control cells; the values in the graph correspond to an average of screenings 1-3.

The screening results of these experiments are shown graphically in FIG. 3, and in the screening data result tables shown in FIG. 5. Control cell line comparisons are shown graphically in FIG. 4, and in the data shown in the summary tables of FIG. 6. In view of these results, it is clear that the lysate sample tested activates human TLR2, 4 and NOD2 at a 1/100 concentration.

Other and further embodiments utilizing one or more aspects of the inventions described above can be devised without departing from the spirit of Applicant's invention. For example, the compositions may include one or more synthetic CpG ODN's, such as the commercially-available Genasense or IMOxine®, in addition to the at least one naturally-occurring CpG ODN and the bacteria lysate fraction. Further, the various methods and embodiments of the methods of manufacture and assembly of the system, as well as location specifications, can be included in combination with each other to produce variations of the disclosed methods and embodiments. Discussion of singular elements can include plural elements and vice-versa.

The order of steps can occur in a variety of sequences unless otherwise specifically limited. The various steps described herein can be combined with other steps, interlineated with the stated steps, and/or split into multiple steps. Similarly, elements have been described functionally and can be embodied as separate components or can be combined into components having multiple functions.

The inventions have been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicants, but rather, in conformity with the patent laws, Applicants intend to fully protect all such modifications and improvements that come within the scope or range of equivalent of the following claims.

The invention claimed is:

1. A composition comprising:
   (a) a lysate and/or cell wall extract from a Gram-positive bacteria, or a pharmaceutically acceptable salt thereof; and
   (b) an immunostimulatory oligodeoxynucleotide (ODN); wherein the composition is formulated for oral delivery; and
   wherein the composition is formulated to dissolve in not less than 1 minute after administration.

2. The composition of claim 1, wherein the Gram-positive bacteria is *Bacillus coagulans, Streptococcus thermophilus, Bifidobacterium animalis, Bifidobacterium infantis, Bifidobacterium longum, Bifidobacterium breve, Lactobacillus sporogenes, Lactobacillus acidophilus, Lactobacillus plantarum, Lactobacillus casei, Lactobacillus delbrueckii* subsp. *bulgaricus, Lactococcus lactis, Streptococcus lactis, Bifidobacterium lactis, Lactobacillus helveticus*, or a combination thereof.

3. The composition of claim 1, wherein the immunostimulatory ODN is a CpG oligodeoxynuclotide (CpG ODN).

4. The composition of claim 3, wherein the CpG ODN is class-A, class-B, class-C, class P, class S, or a combination thereof.

5. The composition of claim 1, further comprising a promoter.

6. The composition of claim 5, wherein the promoter is an amino acid, an N-alkylated amino acid, an N-alkylated peptide, an amino sugar, or a sugar.

7. The composition of claim 6, wherein the promoter is poly-L-lysine, glucosamine, poly-L-arginine, galactosamine, N-acetylmannosamine (NAM; N—Ac-Man), N-acetylglucosamine (NAG; N—Ac-Glc), N,N'-diacetylglucosamine (NAG-NAG; N,N'-diacetylchitobiose), N,N',N'', N'''-tetraacetylglucosamine (NAG-NAG-NAG-NAG; N,N', N'',N'''-tetraacetylchitotetraose), or a combination thereof.

8. The composition of claim 1, further comprising a carrier.

9. The composition of claim 8, wherein the carrier is a binder, a gum base, or a combination thereof.

10. The composition of claim 9, wherein the gum base comprises a hydrophobic polymer and a hydrophilic polymer.

11. The composition of claim 9, wherein the binder is a sugar, a sugar alcohol, or a combination thereof.

12. The composition of claim 1, further comprising a controlled release agent.

13. The composition of claim 12, wherein the controlled release agent has an inherent viscosity ranging from about 0.50 dL/g to about 1.0 dL/g as measured in chloroform.

14. The composition of claim 11, wherein the sugar alcohol is mannitol, sorbitol, xylitol, or a combination thereof.

15. The composition of claim 1, further comprising from about 0 wt. % to about 10 wt. % of a flavoring agent.

16. The composition of claim 1, wherein the dosage form of the composition is a lozenge, a candy, or a dissolving tablet.

17. The composition of claim 1, further comprising a non-steroidal anti-inflammatory drug (NSAID).

18. The composition of claim 8, wherein the average particle size of the lysate or cell wall extract from a Gram-positive bacteria or a pharmaceutically acceptable salt thereof is less than or equal to the average particle size of the carrier.

19. The composition of claim 1, wherein the composition is formulated for buccal or sublingual delivery.

20. The composition of claim 1, wherein the composition is formulated to dissolve in not less than 2 minutes after administration.

* * * * *